US010436803B2

(12) United States Patent
Chen et al.

(10) Patent No.: US 10,436,803 B2
(45) Date of Patent: Oct. 8, 2019

(54) QUANTITATION OF INSULIN BY TANDEM MASS SPECTROMETRY OF INSULIN B CHAIN

(75) Inventors: Zhaohui Chen, Las Flores, CA (US); Nigel Clarke, Oceanside, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 1679 days.

(21) Appl. No.: 13/338,123

(22) Filed: Dec. 27, 2011

(65) Prior Publication Data

US 2012/0164741 A1 Jun. 28, 2012

Related U.S. Application Data

(60) Provisional application No. 61/427,749, filed on Dec. 28, 2010.

(51) Int. Cl.
| | | |
|---|---|---|
| *G01N 33/68* | (2006.01) | |
| *G01N 33/74* | (2006.01) | |
| *G01N 33/49* | (2006.01) | |
| *H01J 49/00* | (2006.01) | |

(52) U.S. Cl.
CPC ............ *G01N 33/74* (2013.01); *G01N 33/49* (2013.01); *G01N 33/6848* (2013.01); *G01N 2333/62* (2013.01); *H01J 49/004* (2013.01)

(58) Field of Classification Search
CPC .............................. G01N 33/74; G01N 33/68
USPC .............................................. 436/86–90, 173
See application file for complete search history.

(56) References Cited

U.S. PATENT DOCUMENTS

| | | | |
|---|---|---|---|
| 5,772,874 | A | 6/1998 | Quinn et al. |
| 5,795,469 | A | 8/1998 | Quinn et al. |
| 5,919,368 | A | 7/1999 | Quinn et al. |
| 5,968,367 | A | 10/1999 | Quinn et al. |
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Koster |
| 6,995,364 | B2 | 2/2006 | Makarov et al. |
| 2005/0103991 | A1 | 5/2005 | Walk et al. |
| 2006/0219558 | A1 | 10/2006 | Hafeman et al. |
| 2008/0118932 | A1 | 5/2008 | Toler et al. |
| 2009/0090856 | A1 | 4/2009 | Grant et al. |
| 2011/0166132 | A1 | 7/2011 | Hitchcock et al. |

FOREIGN PATENT DOCUMENTS

| | | |
|---|---|---|
| CN | 103392219 A | 11/2013 |
| CN | 103454433 A | 12/2013 |
| JP | 2004503749 A | 2/2004 |
| JP | 2005526962 A | 9/2005 |
| WO | 0204957 A2 | 1/2002 |
| WO | 2009133152 A1 | 11/2009 |
| WO | 2012092281 A2 | 7/2012 |
| WO | 2014105858 A1 | 7/2014 |

OTHER PUBLICATIONS

Jia, X. et al, FASEB Journal 2006, 20, E871-E879.*
Regnier, F. et al, Journal of Chromatography A 1996, 750, 3-10.*
Thevis, M. et al, Rapid Communications in Mass Spectrometry 2007, 21, 297-304.*
Ho, E. N. M. et al, Journal of Chromatography A 2008, 1201, 183-190.*
Loo, J. A. et al, Analytical Chemistry 1991, 63, 2488-2499.*
Jespersen, S. et al, Biological Mass Spectrometry 1993, 22, 77-83.*
Zhang, X. et al, Journal of the American Society for Mass Spectrometry 1996, 7, 1211-1218.*
Ewing, N. P. et al, Journal of the American Society for Mass Spectrometry 1999, 10, 928-940.*
Stephenson, J. L. et al, Rapid communications in Mass Spectrometry 1999, 13, 2040-2048.*
Fung, Y. M. E. et al, Angewandte Chemie International Edition 2005, 44, 6399-6403.*
Peng, I. X. et al, Analytical Chemistry 2008, 80, 6995-7003.*
International Search Report issued in PCT/US2011/67397 dated Jun. 28, 2012.
Mannering et al., "The insulin A-chain epitope recognized by human T cells is posttranslationally modified," The Journal of Experimental Medicine, (2005), 202:1191-1197.
International Preliminary Report on Patentability for PCT/US2011/067397 dated Jul. 11, 2013.
Sinner, et al., "A Robust and Easy Method for Simultaneous Quantitation of Glucose and [6,6-d2]Glucose in Human Plasma Using GC-MS," Proceedings of the 52nd ASMS Conference on Mass Spectrometry and Allied Topics, Nashville, Tennessee, May 23-27, 2004. (5 pages).
Extended European Search Report for Application No. 11852467.7, dated Mar. 14, 2014, 6 pages.
Kuuranne T., et al., "Insulins in Equine Urine: Qualitative Analysis by Immunoaffinity Purification and Liquid Chromatography/Tandem Mass Spectrometry for Doping Control Purposes in Horse-Racing," Rapid Communications in Mass Spectrometry, 2008, vol. 22 (3), pp. 355-362.
Thevis M., et al., "Current Role of LC-MS(/MS) in Doping Control," Analytical and Bioanalytical Chemistry, 2007, vol. 388 (7), pp. 1351-1358.
Thevis M., et al., "Doping Control Analysis of Intact Rapid-Acting Insulin Analogues in Human Urine by Liquid Chromatography-Tandem Mass Spectrometry," Analytical Chemistry, 2006, vol. 78 (6), pp. 1897-1903.
Written Opinion for Application No. PCT/US11/67397, dated Jun. 28, 2012, 6 Pages.
Bartolucci et al., "Liquid chromatography tandem mass spectrometic quantitation of sulfamethazine and its metabolites: direct analysis of swine urine by triple quadrupole and by ion trap mass spectrometry," Rapid Commun. Mass Spectrom., (2000), 14:967-973.

(Continued)

*Primary Examiner* — Arlen Soderquist
(74) *Attorney, Agent, or Firm* — Quest Diagnostics, Inc.

(57) ABSTRACT

Methods are described for determining the amount of insulin in a sample. More specifically, mass spectrometric methods are described for detecting and quantifying insulin in a biological sample utilizing purification methods coupled with tandem mass spectrometric or high resolution/high accuracy mass spectrometric techniques.

10 Claims, 26 Drawing Sheets

(56) References Cited

OTHER PUBLICATIONS

Bredehoft et al., "Quantification of human insulin-like growth factor-1 and qualitative detection of its analogues in plasma using liquid chromatoragphy/electrospray ionisation tandem mass spectrometry," Rapid Commun. Mass Spectrom., (2008), 22:477-485.
Darby et al., "A Mass Spectrometric Method for Quantitation of Intact Insulin in Blood Samples," J. Anal. Toxicol., (2001), 25:8-14.
Fierens et al., "Strategies for determination of insulin with tandem electrospray mass spectrometry: implications for other analyte proteins?" Rapid Commun. Mass. Spectrom., (2001), 15(16):1433-1441.
Guedes et al., "Mass Spectrometry Characterization of the Glycation Sites of Bovine Insulin by Tnadem Mass Spectrometry," J. Am. Soc. Mass. Spectrom., (2009), 20:1319-1326.
Le Breton et al., "Direct determination of recombinant bovine somatotropin in plasma from a treated goat by liquid chromatography/high-resolution mass spectrometry," Rapid Commun. Mass Spectrom., (2008), 22:3130-3136.
Manley, et al., "Comparison of II Human Insulin Assays: Implications for Clinical Investigation and Research," Clin. Chem., (2007), 53(5):922-932.
Merchant et al., "Recent advancements in surface-enhanced laser desorption/ionization-time of filght-mass spectrometry," Electrophoresis, (2000), 21:1164-1167.
Olsen et al., "Higher-energy C-trap dissociation for peptide modification analysis," Nature Methods, (2007), 4(9):709-712.
Robb et al., "Atmospheric Pressure Photoionization: An Ionization Method for Liquid Chromatography-Mass Spectrometry," Anal. Chem. (2000), 72:(15):3653-3659.
Rodriguez-Cabaleiro et al., "Pilot Study for the Standardization of Insulin Immunoassays with Isotope Dilution-Liquid Chromatography/Tandem Mass Spectrometry," Clin. Chem., (2007), 53(8):1462-1469.
Schenk et al., "A high confidence, manually validated human blood plasma protein reference set," BMC Med. Genomics, (2008), 1:41.
Stocklin et al., "A stable isotope dilution assay for the in vivo determination of insulin levels in humans by mass spectrometry," Diabetes, (1997), 46(1):44-50.
Thevis et al., "Mass Spectrometric Determination of Insulins and Their Degradation Products in Sports Drug Testing," Mass Spectrom. Reviews, (2008), 27:35-50.
Thevis et al., "Qualitative determination of synthetic analogues of insulin in human plasma by immunoaffinity purification and liquid chromatography-tandem mass spectrometry for doping control purposes," Anal. Chem., (2005), 77(11):3579-3585.
Thomas et al., "Mass spectrometric determination of gonadotrophin-releasing hormone (GnRH) in human urine for doping control purposes by means of LC-ESI-MS/MS," J. Mass Spectrom., (2008), 43:908-915.
Thomas et al., "Mass Spectrometric Identification of Degradation Products of Insulin and Its Long-Acting Analogues in Human Urine for Doping Control Purposes," Anal. Chem. (2007), 79:2518-2524.
Uytfanghe et al., "New liquid chromatography/electrospray ionisation tandem mass spectrometry measurement procedure for quantitative analysis of human insulin in serum," , Rapid Communications in Mass Spectrometry 2007, 21, 819-821.
Wright et al., "Proteinchip surface enhanced laser desorption/ionization (SELDI) mass spectrometry: a novel protein biochip technology for detection of prostate cancer biomarkers in complex protein mixtures," Prostate Cancer and Prostatic Diseases, (1999), 2:264-276.
Zimmer et al., "Comparison of turbulent-flow with automated solid-phase extraction in 96-well plates and liquid-liquid extraction used as plasma sample preparation techniques for liquid chromatography-tandem mass spectrometry," J. Chromatogr. A, (1999), 854:23-35.
Non-Final Office Action dated Jan. 22, 2016 for U.S. Appl. No. 14/063,956 filed Oct. 25, 2013.
Jonassen P., et al., "Single-Step Trypsin Cleavage of a Fusion Protein to Obtain Human Insulin and Its C Peptide," European Journal of Biochemistry, Mar. 1996, vol. 236 (2), pp. 656-661.
Kippen A.D., et al., "Development of an Isotope Dilution Assay for Precise Determination of Insulin, C-Peptide, and Proinsulin Levels in Non-diabetic and Type II Diabetic Individuals With Comparison to Immunoassay," The Journal of Biological Chemistry, May 1997, vol. 272 (19), pp. 12513-12522.
Landreh M., et al., "Proinsulin C-Peptide Interferes With Insulin Fibril Formation," Biochemical and Biophysical Research Communications, Feb. 2012, vol. 418 (3), pp. 489-493.
Non-Final Office Action dated May 23, 2018 for U.S. Appl. No. 15/059,247 filed Mar. 2, 2016.
Waters QTOF Ultima ESI, Mass Spectrometry Lab, School of Chemical Sciences, 2002, 2 pages. [retrieved on May 18, 2018]. Retrieved from the Internet[URL: http://www.scs.illinois.edu/massSpec/instrum/qtof.php].
European Search Report for Application No. 17189034.6 dated Oct. 19, 2017.
Stewart K.W., et al., "A Simple and Rapid Method for Identifying and Semi-quantifying Peptide Hormones in Isolated Pancreatic Islets by Direct-Tissue Matrix-Assisted Laser Desorption Ionization Time-of-Flight Mass Spectrometry," Rapid Communications in Mass Spectrometry, 2011, vol. 25 (22), pp. 3387-3395.
Cham B.E., et al., "A Solvent System for Delipidation of Plasma or Serum Without Protein Precipitation," Journal of Lipid Research, Mar. 1976, vol. 17 (2), pp. 176-181.
European Search Report for Application No. 16759509.9 dated Jul. 13, 2018.
Landreh M., et al., "Insulin, Islet Amyloid Polypeptide and C-Peptide Interactions Evaluated by Mass Spectrometric Analysis," Rapid Communications in Mass Spectrometry, 2014, vol. 28 (2), pp. 178-184.
Extended European Search Report for Application No. EP18209927.5, dated Apr. 17, 2019, 8 pages.
Extended European Search Report for Application No. EP16176190.3, dated Sep. 29, 2016, 7 pages.
International Search Report and Written Opinion for Application No. PCT/US2016/020723, dated Jul. 25, 2016, 19 pages.

\* cited by examiner

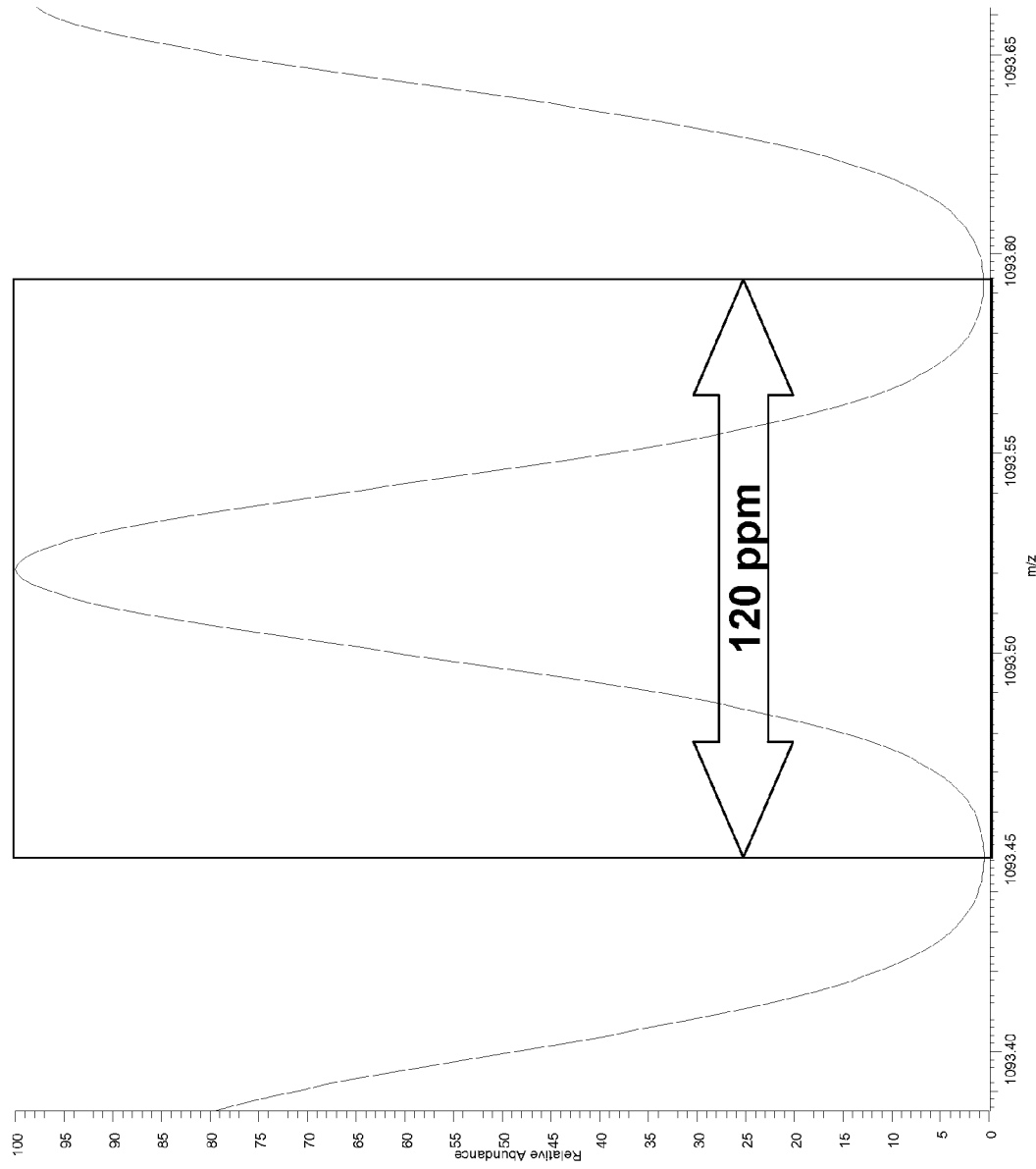

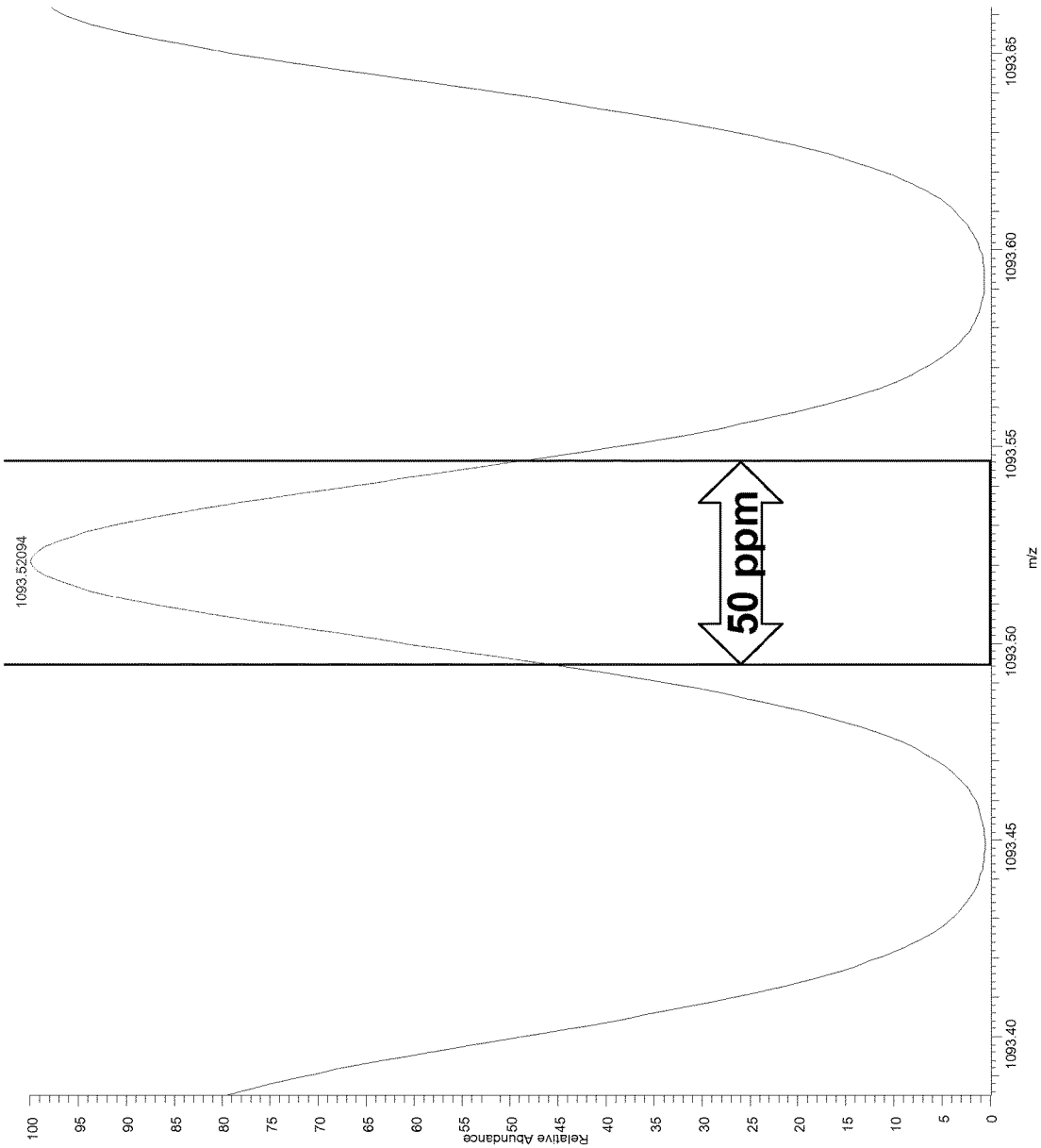

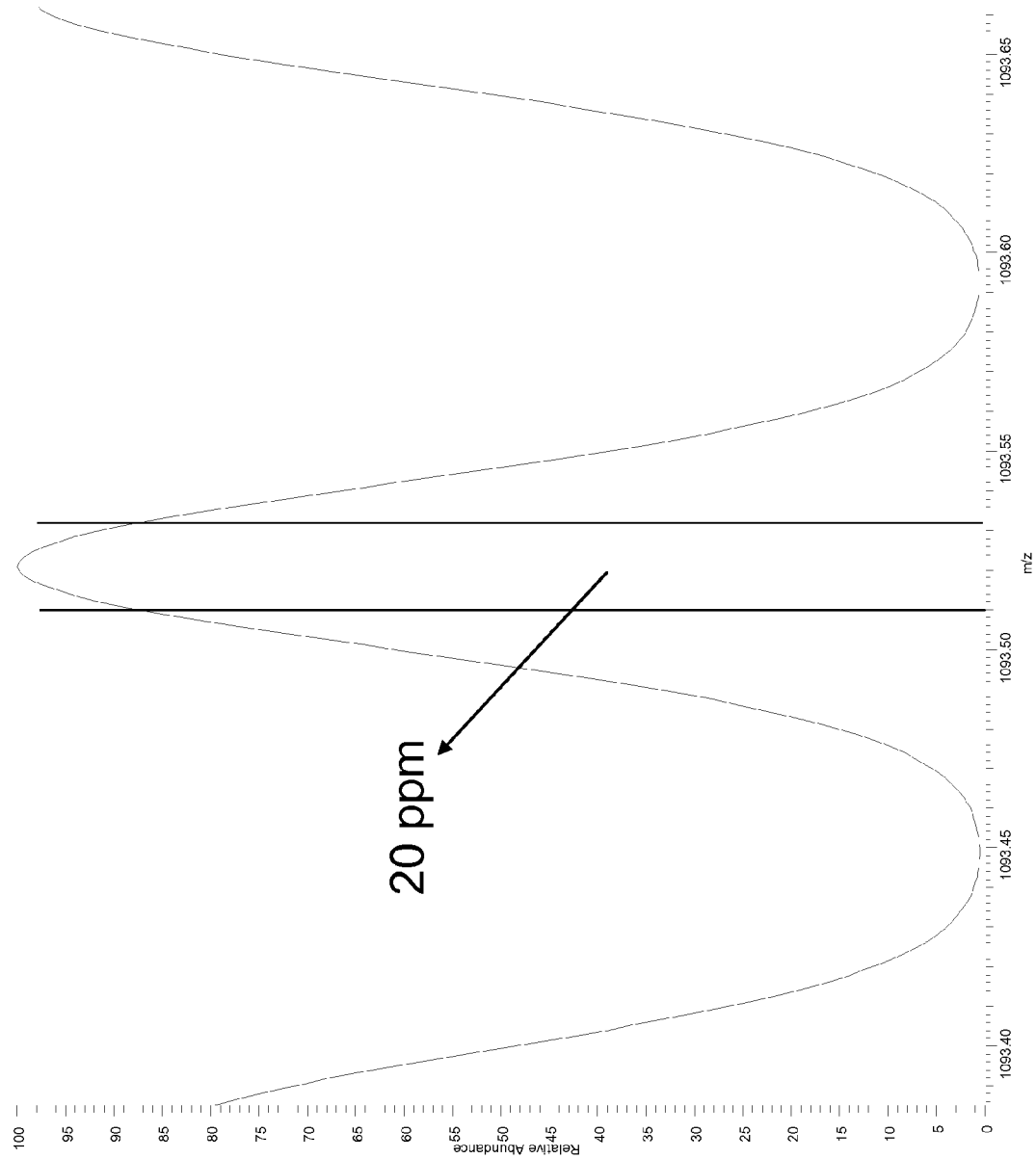

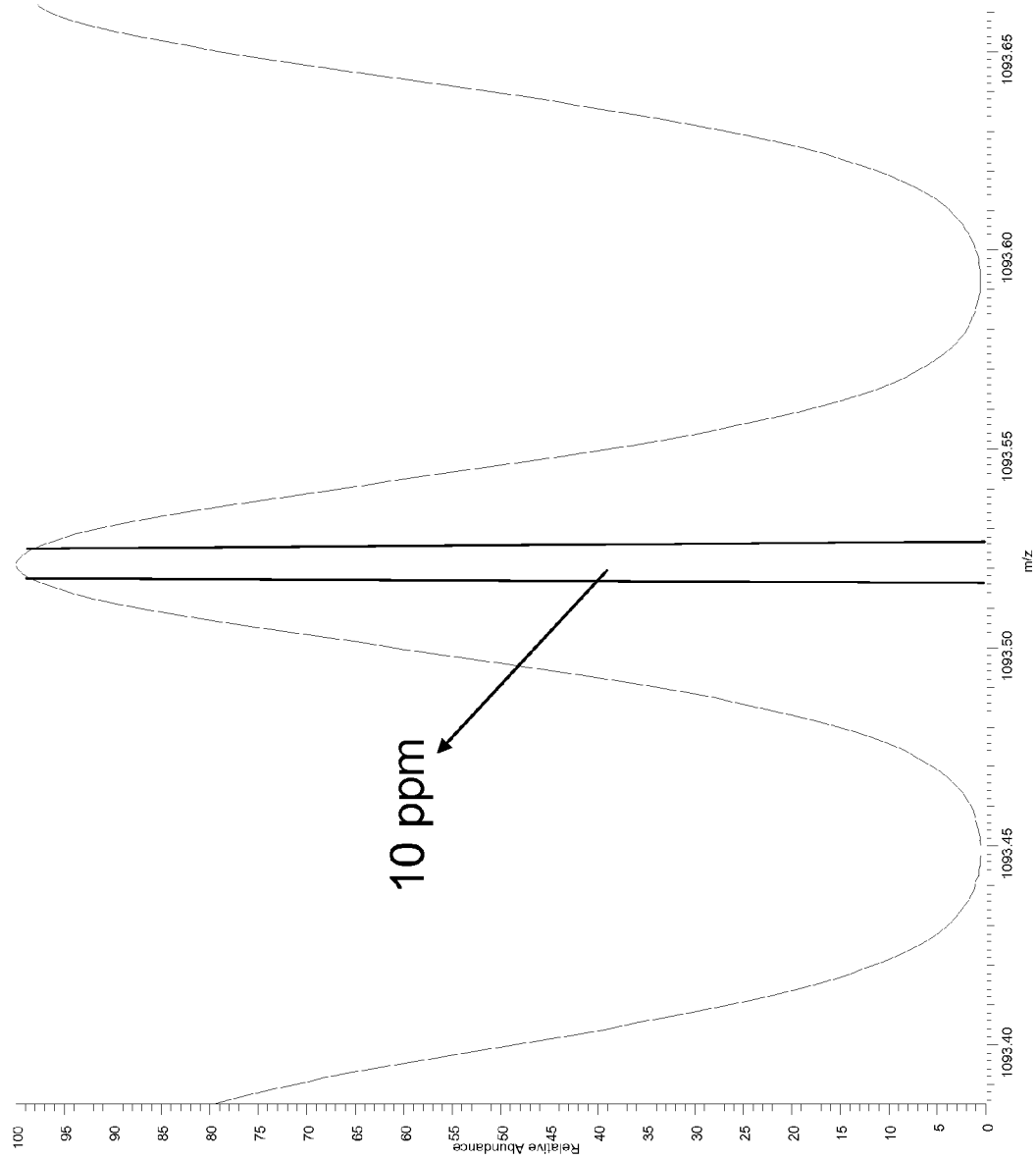

Figure 5
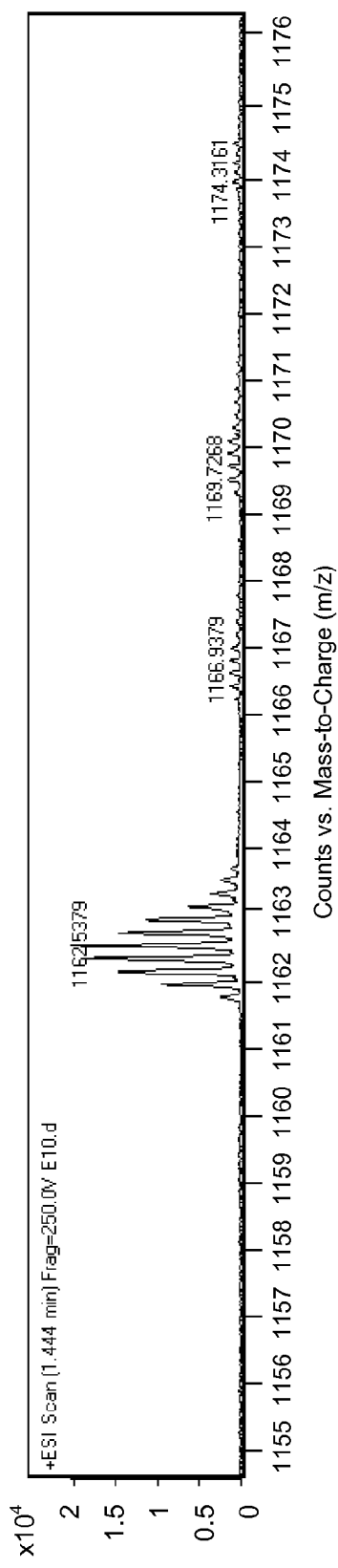
A
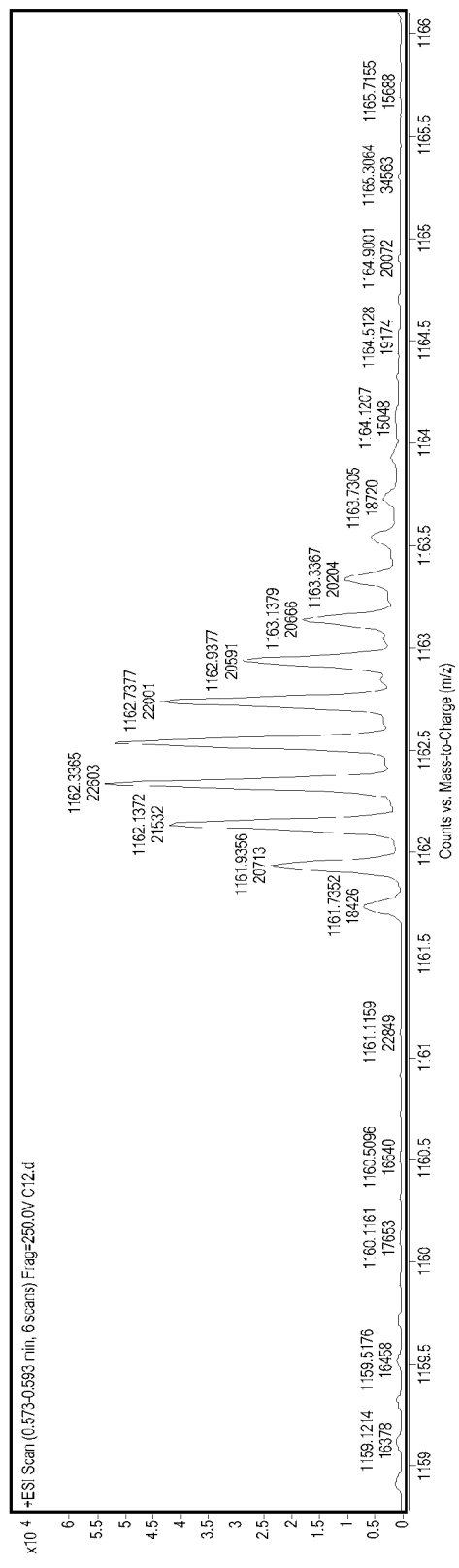
B

QUANTITATION OF INSULIN BY TANDEM MASS SPECTROMETRY OF INSULIN B CHAIN

RELATED PATENT APPLICATIONS

This application claims the benefit of U.S. Provisional Application No. 61/427,749 filed Dec. 28, 2010, which is incorporated herein by reference in its entirety and for all purposes.

FIELD OF THE INVENTION

The invention relates to the quantitative measurement of insulin. In a particular aspect, the invention relates to methods for quantitative measurement of insulin by mass spectrometry.

BACKGROUND OF THE INVENTION

The following description of the background of the invention is provided simply as an aid in understanding the invention and is not admitted to describe or constitute prior art to the invention.

Insulin is a small peptide consisting of fifty-one amino acids in two chains, denoted the A chain and the B chain, linked by disulfide bridges between cysteine residues. Human insulin has a molar mass of about 5607.4 amu. The A chain has twenty one amino acids and the B chain has thirty amino acids.

Insulin is a hormone that is central to regulating fat and steroid metabolism in the body. When blood sugar levels rise following a meal, insulin is released into the bloodstream and allows for the transport of glucose from the circulation into cells.

A deficiency in insulin production or utilization results in diabetes mellitus. Insulin is often administered for the treatment of diabetes. Diabetes and its complications represent a major public health issue. Thus, quantitation of insulin in diabetic and pre-diabetic patient samples is important both as a diagnostic tool and for monitoring patient treatment.

Immunological techniques have been widely used for insulin quantitation (see, e.g., Manley, et al., *Clin Chem.*, 2007, 53:922-32), and several mass spectrometric methods have been reported for detecting and/or quantitating insulin. See, e.g., Stocklin, R., et al., *Diabetes* 1997, 46:44-50 (reporting quantitation of insulin in serum samples by immunoaffinity chromatography-solid phase extraction-HPLC-single mass spectrometry); Darby, S. M., et al., *J. Anal Toxicol* 2001, 25:8-14 (reporting SPE-HPLC-MS quantitation of insulin in plasma at above physiological levels); Fierens, C., et al., *Rapid Commun. Mass Spectrom.* 2001, 15:1433-41 (reporting detection of insulin in water solutions by HPLC-(ESI) MS/MS); Magnes, C., et al., $52^{nd}$ ASMS Conference, May 2004 (reporting quantitation of insulin in serum with high resolution/high accuracy mass spectrometry); Thevis, M., et al., *Anal. Chem.*, 2005, 77:3579-85 (reporting immunoaffinity chromatography-solid phase extraction-HPLC-tandem mass spectrometric methods for quantitation of insulin and detection of insulin B-chain from plasma); Thevis, M., et al., *Anal. Chem.*, 2006, 77:3579-85 and Thomas, A., et al., *Anal. Chem.*, 2007, 79:2518-24 (reporting solid phase extraction-immunoaffinity chromatography-solid phase extraction-HPLC-tandem mass spectrometric methods for quantitation of insulin and detection of insulin B-chain from plasma); Uytfanghe, K., et al., *Rapid Comm Mass Spectrom.*, 2007, 21:819-821 (reporting immunoaffinity chromatography-solid phase extraction-HPLC-tandem mass spectrometric methods for quantitation of insulin from serum); Rodríguez-Cabaleiro, D., et al., *Clin Chem.*, 2007, 53:1462-69 (reporting immunoaffinity chromatography-solid phase extraction-HPLC-tandem mass spectrometric methods for quantitation of insulin and detection of insulin B-chain from plasma); Thevis, M., et al., *Mass Spectrom. Reviews*, 2008, 27:35-50 (reporting immunoaffinity chromatography-solid phase extraction-HPLC-tandem mass spectrometric methods for quantitation of insulin and detection of insulin B-chain from plasma); and Guedes, S., *J. Am. Soc Mass Spectrom*, 2009, 20:1319-26.

SUMMARY OF THE INVENTION

The present invention provides methods for determining the amount of insulin in a sample by mass spectrometry.

In one aspect, the methods utilize tandem mass spectrometry. In some tandem mass spectrometry embodiments, the methods are for determining the amount of insulin in a biological sample when taken from a human. In some embodiments, the methods include: (a) subjecting a sample to solid phase extraction (SPE) and high performance liquid chromatography (HPLC) to obtain a fraction enriched in insulin from the sample; (b) subjecting the enriched insulin to an ionization source under conditions suitable to generate one or more insulin ions detectable by mass spectrometry; (c) determining the amount of one or more insulin ions by tandem mass spectrometry, wherein said sample is not subjected to immunopurification prior to ionization. In these embodiments, the amount of the one or more ions determined in step (c) is used to determine the amount of insulin in the sample.

In some embodiments, the sample is subjected to acidic conditions prior to ionization in positive ion mode. In some related embodiments, subjecting the sample to acidic conditions comprises subjecting enriched insulin to formic acid. In some related embodiments, one or more ions determined in step (c) comprise an insulin precursor ion selected from the group consisting of ions with a mass to charge ratio (m/z) of 1162.5±0.5 and 968.9±0.5. In further related embodiments, one or more ions determined in step (c) comprise one or more fragment ions selected from the group consisting of ions with m/z of 226.2±0.5 and 135.9±0.5. In other related embodiments, one or more fragment ions comprise one or more fragment ions from an insulin precursor ion with m/z of 1162.5±0.5 and one or more fragment ions from an insulin precursor ion with m/z of 968.9±0.5. In related embodiments, one or more fragment ions from each precursor ion comprise one or more fragment ions selected from the group consisting of ions with m/z of 226.2±0.5 and 135.9±0.5.

In some embodiments, the sample is subjected to basic conditions prior to ionization in positive ion mode. In some related embodiments, subjecting the sample to basic conditions comprises subjecting the sample to ammonia. In some related embodiments, one or more ions determined in step (c) comprise an insulin precursor ion selected from the group consisting of ions with m/z of 1453.8±0.5 and 1163.0±0.5. In further related embodiments, one or more ions determined in step (c) comprise one or more fragment ions selected from the group consisting of ions with m/z of 226.2±0.5 and 135.9±0.5. In other related embodiments, one or more fragment ions comprise one or more fragment ions from an insulin precursor ion with m/z of 1453.8 and one or more fragment ions from an insulin precursor ion with a mass to charge ratio of 1163.0±0.5.

In some embodiments utilizing tandem mass spectrometry for determining the amount of insulin in a sample, the methods include: (a) enriching insulin in a sample by an extraction technique; (b) subjecting the purified insulin from step (a) to high performance liquid chromatography (HPLC) to obtain a fraction enriched in insulin from the sample; (c) subjecting the enriched insulin to an ionization source under conditions suitable to generate an insulin precursor ion detectable by mass spectrometry, wherein the insulin precursor ion has m/z of 1162.5±0.5; (d) subjecting the insulin precursor ion to collision induced dissociation at a collision energy within the range of about 40 to 70 eV to generate one or more fragment ions detectable by mass spectrometry; and (e) determining the amount of one or more of the fragment ions by mass spectrometry. In these embodiments, the amount of ions determined in step (e) is related to the amount of insulin in said sample. In some embodiments, the extraction technique is solid phase extraction (SPE).

In some embodiments, the sample is subjected to acidic conditions prior to ionization in positive ion mode. In some related embodiments, subjecting the sample to acidic conditions comprises subjecting the sample to formic acid. In alternative embodiments, the sample is subjected to basic conditions prior to ionization. In some related embodiments, subjecting the sample to basic conditions comprises ammonia.

In some embodiments, the collision energy is within the range of about 40 to 60 eV; such as within the range of about 40 to 50 eV. In some embodiments, one or more fragment ions generated in step (d) comprise one or more ions selected from the group consisting of ions with m/z of 226.2±0.5 and 135.9±0.5.

In some embodiments that utilize tandem mass spectrometry for determining the amount of insulin in a biological sample when taken from a human, the methods include: (a) subjecting a sample to conditions suitable to generate insulin A chains from insulin; (b) subjecting the sample from step (a) to solid phase extraction (SPE) and high performance liquid chromatography (HPLC) to obtain a fraction enriched in insulin A chains; (c) subjecting the enriched insulin A chains to an ionization source under conditions suitable to generate one or more insulin A chain ions detectable by mass spectrometry; (d) determining the amount of one or more insulin A chain ions by tandem mass spectrometry. In these embodiments, the amount of ions determined in step (d) is related to the amount of insulin in said sample.

In some related embodiments, the sample is subjected to acidic conditions prior to ionization in positive ion mode. In some related embodiments, subjecting the sample to acidic conditions comprises subjecting said sample to formic acid. In some embodiments, the insulin A chains generated in step (a) are not chemically modified prior to ionization. In some related embodiments, the one or more ions determined in step (d) comprise an insulin A chain precursor ion selected from the group consisting of ions with m/z of 1192.9±0.5 and 795.4±0.5. In some related embodiments, the one or more ions determined in step (d) comprise one or more fragment ions selected from the group of ions with m/z of 513.0±0.5, 399.0±0.5, 236.0 0.5, and 133.0±0.5. In some related embodiments, the one or more ions determined in step (d) comprise one or more fragment ions from an insulin A chain precursor ion with m/z of 1192.9±0.5 and one or more fragment ions from an insulin A chain precursor ion with m/z of 795.4±0.5. In some related embodiments, the one or more fragment ions from each precursor ion comprise one or more fragment ions selected from the group consisting of ions with m/z of 513.0±0.5, 399.0±0.5, 236.0±0.5, and 133.0±0.5.

In alternative embodiments, the methods further comprise chemically modifying the insulin A chains generated in step (a) prior to ionization. In some embodiments, chemical modification comprises alkylating the insulin A chains. In further related embodiments, one or more ions determined in step (d) comprise an alkylated insulin A chain precursor ion selected from the group consisting of ions with m/z of 1306.0±0.5 and 871.0±0.5. In other related embodiments, one or more ions determined in step (d) comprise one or more fragment ions selected from the group of ions with m/z of 570.0±0.5, 456.0±0.5, 293.0±0.5, and 133.0±0.5. In other related embodiments, one or more ions determined in step (d) comprise one or more fragment ions from an alkylated insulin A chain precursor ion with m/z of 1306.0±0.5 and one or more fragment ions from an alkylated insulin A chain precursor ion with m/z of 871.0±0.5. In some related embodiments, one or more fragment ions from each alkylated precursor ion comprise one or more fragment ions selected from the group consisting of ions with m/z of 570.0±0.5, 456.0±0.5, 293.0±0.5, and 133.0±0.5.

In some embodiments, tandem mass spectrometry is utilized to determine the amount of insulin in a biological sample. In these embodiments, the methods include: (a) subjecting a sample to conditions suitable to generate insulin B chains from insulin; (b) processing the sample from step (a) to obtain a fraction enriched in insulin B chains; (c) subjecting the enriched insulin B chains to an ionization source under conditions suitable to generate one or more insulin B chain ions detectable by mass spectrometry; (d) determining the amount of one or more insulin B chain ions by tandem mass spectrometry. In these embodiments, the amount of ions determined in step (d) is related to the amount of insulin in the sample.

In some embodiments, the processing of step (b) includes enriching insulin B chains by solid phase extraction (SPE), high performance liquid chromatography (HPLC), or both. In some related embodiments where both SPE and HPLC are used, the two enrichment techniques may be conducted in an on-line fashion.

In some embodiments, the biological sample comprises a human plasma or serum sample. In some related embodiments, the amount of insulin determined is the amount of insulin present in the sample when taken from the human.

In some embodiments, the ionization source is an electrospray ionization (ESI) source, such as a heated ESI source.

In some embodiments, the sample is subjected to acidic conditions prior to ionization in positive ion mode. In some related embodiments, subjecting the sample to acidic conditions comprises subjecting said sample to formic acid.

In some embodiments, the insulin B chains are not chemically modified prior to ionization. In some related embodiments, one or more ions determined in step (d) comprise an insulin B chain precursor ion selected from the group consisting of ions with m/z of 1144.2±0.5, 858.3±0.5, and 686.8±0.5. In some related embodiments, one or more ions determined in step (d) comprise one or more fragment ions selected from the group consisting of ions with m/z of 906.0±0.5, 825.0±0.5, 768.5±0.5, 753.0±0.5, 703.0±0.5, 345.0±0.5 and 226.2±0.5, such as the group consisting of ions with m/z of 768.5±0.5, 753.0±0.5, 345.0±0.5 and 226.2±0.5, such as the group consisting of ions with m/z of 768.5±0.5 and 753.0±0.5. In some embodiments, one or more ions determined in step (d) comprise two or more fragment ions selected from the group consisting of a fragment ion from an insulin B chain precursor ion with m/z of 1144.2±0.5, a fragment ion from an insulin B chain precursor ion with m/z of 858.3±0.5, and a fragment ion from an insulin B chain precursor ion with m/z of 686.8±0.5.

In some embodiments, tandem mass spectrometry comprises generating a human insulin B chain precursor ion with mass to charge ratio (m/z) of 686.8±0.5 and fragmenting the precursor ion into one or more fragment ions selected from the group consisting of ions with m/z of 906.0±0.5, 825.0±0.5, 768.5±0.5, 753.0±0.5, 703.0±0.5, 345.0±0.5 and 226.2±0.5, such as one or more fragment ions selected from the group consisting of 768.5±0.5 and 753.0±0.5.

In some embodiments, tandem mass spectrometry comprises fragmenting a precursor ion with a collision energy within the range of 10 to 25 V, inclusive.

In alternative embodiments, the insulin B chains are chemically modified prior to ionization. In some embodiments, chemical modification comprises alkylating said insulin B chains. In some embodiments, one or more ions determined in step (d) comprise an alkylated insulin B chain precursor ion selected from the group consisting of ions with m/z of 1181.9±0.5, 886.9±0.5, and 709.8±0.5. In some embodiments, one or more ions determined in step (d) comprise one or more fragment ions selected from the group of ions with m/z of 345.0±0.5 and 226.2±0.5. In some embodiments, one or more ions determined in step (d) comprise two or more fragment ions selected from the group consisting of a fragment ion from an alkylated insulin B chain precursor ion with a mass to charge ratio (m/z) of 1181.9±0.5, a fragment ion from an alkylated insulin B chain precursor ion with m/z of 886.9±0.5, and a fragment ion from an alkylated insulin B chain precursor ion with m/z of 709.8±0.5. In some related embodiments, the fragment ion from each precursor ion comprises an ion selected from the group consisting of ions with m/z of 345.0±0.5 and 226.2±0.5.

In a second aspect, certain methods presented herein utilize high resolution/high accuracy mass spectrometry to determine the amount of insulin in a sample. In some embodiments utilizing high accuracy/high resolution mass spectrometry, the methods include:
(a) subjecting insulin from a sample to an ionization source under conditions suitable to generate multiply charged insulin ions, wherein the insulin ions are detectable by mass spectrometry; and
(b) determining the amount of one or more multiply charged insulin ions by high resolution/high accuracy mass spectrometry. In these embodiments, the amount of one or more ions determined in step (b) is related to the amount of insulin in the sample. In some embodiments, high resolution/high accuracy mass spectrometry is conducted at a FWHM of 10,000 and a mass accuracy of 50 ppm. In some embodiments, high resolution/high accuracy mass spectrometry is conducted with a high resolution/high accuracy time-of-flight (TOF) mass spectrometer. In some embodiments, the ionization conditions comprise ionization of insulin under acidic conditions. In some related embodiments, the acidic conditions comprise treatment of said sample with formic acid prior to ionization. In some embodiments, the multiply charged insulin ions are selected from the group consisting of 4+, 5+, and 6+ charged insulin ions.

In some embodiments, one or more insulin ions in a 6+ charge state comprise one or more ions with m/z within the range of about 968.8±1.5. In some embodiments, one or more insulin ions in a 6+ charge state comprise one or more ions selected from the group consisting of ions with m/z of 968.28±0.1, 968.45±0.1, 968.62±0.1, 968.79 0.1, 968.95±0.1, 969.12±0.1, 969.28±0.1, 969.45±0.1, 969.61±0.1; such as an ions with m/z of 968.95±0.1.

In some embodiments, one or more insulin ions in a 5+ charge state comprise one or more ions with m/z within the range of about 1162.5±1.0. In some embodiments, one or more insulin ions in a 5+ charge state comprise one or more ions selected from the group consisting of ions with m/z of 1161.72±0.1, 1161.92±0.1, 1162.12±0.1, 1162.32±0.1, 1162.52±0.1, 1162.72±0.1, 1162.92±0.1, 1163.12±0.1, 1163.32±0.1; such as an ion with m/z of 1162.54±0.1.

In some embodiments, one or more insulin ions in a 4+ charge state comprise one or more ions with m/z within the range of about 1452.9±0.8.

In any of the methods described herein, the sample may comprise a biological sample. In some embodiments, the biological sample may comprise a biological fluid such as urine, plasma, or serum. In some embodiments, the biological sample may comprise a sample from a human; such as from an adult male or female, or juvenile male or female, wherein the juvenile is under age 18, under age 15, under age 12, or under age 10. The human sample may be analyzed to diagnose or monitor a disease state or condition, or to monitor therapeutic efficacy of treatment of a disease state or condition. In some related embodiments, the methods described herein may be used to determine the amount of insulin in a biological sample when taken from a human.

In embodiments utilizing tandem mass spectrometry, tandem mass spectrometry may be conducted by any method known in the art, including for example, multiple reaction monitoring, precursor ion scanning, or product ion scanning.

In some embodiments, tandem mass spectrometry comprises fragmenting a precursor ion into one or more fragment ions. In embodiments where the amounts of two or more fragment ions are determined, the amounts may be subject to any mathematical manipulation known in the art in order to relate the measured ion amounts to the amount of insulin in the sample. For example, the amounts of two or more fragment ions may be summed as part of determining the amount of insulin in the sample.

In any of the methods described herein, the analyte of interest (e.g., insulin, chemically modified or unmodified insulin A chains, or chemically modified or unmodified insulin B chains) may be purified from a sample by high performance liquid chromatography (HPLC) prior to ionization. In any of the methods described herein, the analyte of interest may be purified from a sample by an extraction technique, such as subjecting the sample to a solid phase extraction (SPE) column. In some embodiments, the extraction technique is not an immunopurification technique. Specifically, in some embodiments, the SPE column is not an immunoaffinity column. In some embodiments, immunopurification is not used at any point in the method. In some embodiments; an extraction technique and HPLC may be performed in an on-line fashion to allow for automated sample processing and analysis.

In some embodiments, the high resolution/high accuracy mass spectrometry is conducted at a resolving power (FWHM) of greater than or equal to about 10,000, such as greater than or equal to about 15,000, such as greater than or equal to about 20,000, such as greater than or equal to about 25,000. In some embodiments, the high resolution/high accuracy mass spectrometry is conducted at an accuracy of less than or equal to about 50 ppm, such as less than or equal to about 20 ppm, such as less than or equal to about 10 ppm, such as less than or equal to about 5 ppm; such as less than or equal to about 3 ppm. In some embodiments, high resolution/high accuracy mass spectrometry is conducted at a resolving power (FWHM) of greater than or equal to about 10,000 and an accuracy of less than or equal to about 50 ppm. In some embodiments, the resolving power is greater than about 15,000 and the accuracy is less than or equal to about 20 ppm. In some embodiments, the resolving power is greater than or equal to about 20,000 and the accuracy is less than or equal to about 10 ppm; preferably resolving power is greater than or equal to about 20,000 and accuracy is less than or equal to about 5 ppm, such as less than or equal to about 3 ppm.

In some embodiments, the high resolution/high accuracy mass spectrometry may be conducted with an orbitrap mass spectrometer, a time of flight (TOF) mass spectrometer, or a Fourier transform ion cyclotron resonance mass spectrometer (sometimes known as a Fourier transform mass spectrometer).

In some embodiments, the one or more insulin ions detectable by high resolution/high accuracy mass spectrometry are one or more ions selected from the group consisting of ions with m/z within the ranges of about 1452.9±0.8, 1162.5±1 and 968.8±1.5. Ions within these ranges correspond to insulin ions with charges of 4+, 5+, and 6+, respectively. Monoisotopic ions with these charges predominantly fall within the cited m/z ranges. However, lower abundance naturally occurring isotopic variants may occur outside of these ranges. Insulin ions within the range of 1162.5±1 preferably comprise an insulin ion with m/z of about 1161.72±0.1, 1161.92±0.1, 1162.12±0.1, 1162.32±0.1, 1162.52±0.1, 1162.72±0.1, 1162.92±0.1, 1163.12±0.1, 1163.32±0.1; such as an ion with m/z of 1162.54±0.1. Insulin ions within the range of 968.8±1.5 preferably comprise an insulin ion with m/z of about 968.28±0.1, 968.45±0.1, 968.62±0.1, 968.79±0.1, 968.95±0.1, 969.12±0.1, 969.28±0.1, 969.45±0.1, 969.61±0.1; such as an ions with m/z of 968.95±0.1. In some embodiments, relating the amount of one or more insulin ions detected by mass spectrometry to the amount of an insulin protein in the sample includes comparison to an internal standard; such as a human or non-human insulin protein. The internal standard may optionally be isotopically labeled.

In any of the methods presented herein, the sample may comprise a biological sample; preferably a body fluid sample, including, for example, plasma or serum.

Mass spectrometry (either tandem or high resolution/high accuracy) may be performed in positive ion mode. Alternatively, mass spectrometry may be performed in negative ion mode. Various ionization sources, including for example atmospheric pressure chemical ionization (APCI) or electrospray ionization (ESI), may be used to ionize insulin. In some embodiments, insulin, and/or chemically modified or unmodified insulin A chain or insulin B chain are ionized by ESI in positive ion mode.

In any method presented herein, a separately detectable internal standard may be provided in the sample, the amount of which is also determined in the sample. In embodiments utilizing a separately detectable internal standard, all or a portion of both the analyte of interest and the internal standard present in the sample is ionized to produce a plurality of ions detectable in a mass spectrometer, and one or more ions produced from each are detected by mass spectrometry. In these embodiments, the presence or amount of ions generated from the analyte of interest may be related to the presence of amount of analyte of interest in the sample by comparison to the amount of internal standard ions detected.

Alternatively, the amount of insulin in a sample may be determined by comparison to one or more external reference standards. Exemplary external reference standards include blank plasma or serum spiked with human or non-human insulin, a synthetic insulin analogue, or an isotopically labeled variant thereof.

In some embodiments, the methods are capable of determining the amount of insulin in a sample at levels within the range of about 10 µIU/mL to 500 µIU/mL (equivalent to about 60 pmol/L to 3000 pmol/L, or about 0.35 ng/mL to 17.4 ng/mL), inclusive.

As used herein, unless otherwise stated, the singular forms "a," "an," and "the" include plural reference. Thus, for example, a reference to "a protein" includes a plurality of protein molecules.

As used herein, the terms "purification", "purifying", and "enriching" do not refer to removing all materials from the sample other than the analyte(s) of interest. Instead, these terms refer to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "immunopurification" or "immunopurify" refers to a purification procedure that utilizes antibodies, including polyclonal or monoclonal antibodies, to enrich the one or more analytes of interest. Immunopurification can be performed using any of the immunopurification methods well known in the art. Often the immunopurification procedure utilizes antibodies bound, conjugated or otherwise attached to a solid support, for example a column, well, tube, gel, capsule, particle or the like. Immunopurification as used herein includes without limitation procedures often referred to in the art as immunoprecipitation, as well as procedures often referred to in the art as affinity chromatography or immunoaffinity chromatography.

As used herein, the term "immunoparticle" refers to a capsule, bead, gel particle or the like that has antibodies bound, conjugated or otherwise attached to its surface (either on and/or in the particle). In certain preferred embodiments, immunoparticles are sepharose or agarose beads. In alternative preferred embodiments, immunoparticles comprise glass, plastic or silica beads, or silica gel.

As used herein, the term "anti-insulin antibody" refers to any polyclonal or monoclonal antibody that has an affinity for insulin. In various embodiments the specificity of insulin antibodies to chemical species other than insulin may vary; for example in certain preferred embodiments the anti-insulin antibodies are specific for insulin and thus have little or no affinity for chemical species other than insulin, whereas in other preferred embodiments the anti-insulin antibodies are non-specific and thus bind certain chemical species other than insulin.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In preferred embodiments, the sample comprises a body fluid sample from human; preferably plasma or serum.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit strong cation exchange and hydrophobic retention.

Generally, the affinity of a SPE column packing material for an analyte may be due to any of a variety of mechanisms, such as one or more chemical interactions or an immunoaffinity interaction. In some embodiments, SPE of insulin is conducted without the use of an immunoaffinity column packing material. That is, in some embodiments, insulin is purified from a sample by a SPE column that is not an immunoaffinity column.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in substantially straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 µm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means 10%. In a preferred embodiment the analytical column contains particles of about 5 µm in diameter.

As used herein, the terms "on-line" and "inline", for example as used in "on-line automated fashion" or "on-line extraction", refers to a procedure performed without the need for operator intervention. In contrast, the term "off-line" as used herein refers to a procedure requiring manual intervention of an operator. Thus, if samples are subjected to precipitation and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer, a mass analyzer, and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, "high resolution/high accuracy mass spectrometry" refers to mass spectrometry conducted with a mass analyzer capable of measuring the mass to charge ratio of a charged species with sufficient precision and accuracy to confirm a unique chemical ion. Confirmation of a unique chemical ion is possible for an ion when individual isotopic peaks from that ion are readily discernable. The particular resolving power and mass accuracy necessary to confirm a unique chemical ion varies with the mass and charge state of the ion.

As used herein, the term "resolving power" or "resolving power (FWHM)" (also known in the art as "$m/\Delta m_{50\%}$") refers to an observed mass to charge ratio divided by the width of the mass peak at 50% maximum height (Full Width Half Maximum, "FWHM"). The effect of differences in resolving power is illustrated in FIGS. 1A-C, which show theoretical mass spectra of an ion with a m/z of about 1093. FIG. 1A shows a theoretical mass spectrum from a mass analyzer with resolving power of about 3000 (a typical operating condition for a conventional quadrupole mass analyzer). As seen in FIG. 1A, no individual isotopic peaks are discernable. By comparison, FIG. 1B shows a theoretical mass spectrum from a mass analyzer with resolving power of about 10,000, with clearly discernable individual isotopic peaks. FIG. 1C shows a theoretical mass spectrum from a mass analyzer with resolving power of about 12,000. At this highest resolving power, the individual isotopic peaks contain less than 1% contribution from baseline.

As used herein a "unique chemical ion" with respect to mass spectrometry refers a single ion with a single atomic makeup. The single ion may be singly or multiply charged.

As used herein, the term "accuracy" (or "mass accuracy") with respect to mass spectrometry refers to potential deviation of the instrument response from the true m/z of the ion investigated. Accuracy is typically expressed in parts per million (ppm). The effect of differences in mass accuracy is illustrated in FIGS. 2A-D, which show the boundaries of potential differences between a detected m/z and the actual m/z for a theoretical peak at m/z of 1093.52094. FIG. 2A shows the potential range of detected m/z at an accuracy of 120 ppm. By contrast, FIG. 2B shows the potential range of detected m/z at an accuracy of 50 ppm. FIGS. 2C and 2D show the even narrower potential ranges of detected m/z at accuracies of 20 ppm and 10 ppm.

High resolution/high accuracy mass spectrometry methods of the present invention may be conducted on instruments capable of performing mass analysis with FWHM of greater than 10,000, 15,000, 20,000, 25,000, 50,000, 100,000, or even more. Likewise, methods of the present invention may be conducted on instruments capable of performing mass analysis with accuracy of less than 50 ppm, 20 ppm, 15 ppm, 10 ppm, 5 ppm, 3 ppm, or even less. Instruments capable of these performance characteristics may incorporate certain orbitrap mass analyzers, time-of-flight ("TOF") mass analyzers, or Fourier-transform ion cyclotron resonance mass analyzers. In preferred embodiments, the methods are carried out with an instrument which includes an orbitrap mass analyzer or a TOF mass analyzer.

The term "orbitrap" describes an ion trap consisting of an outer barrel-like electrode and a coaxial inner electrode. Ions are injected tangentially into the electric field between the electrodes and trapped because electrostatic interactions between the ions and electrodes are balanced by centrifugal forces as the ions orbit the coaxial inner electrode. As an ion orbits the coaxial inner electrode, the orbital path of a trapped ion oscillates along the axis of the central electrode at a harmonic frequency relative to the mass to charge ratio of the ion. Detection of the orbital oscillation frequency allows the orbitrap to be used as a mass analyzer with high accuracy (as low as 1-2 ppm) and high resolving power (FWHM) (up to about 200,000). A mass analyzer based on an orbitrap is described in detail in U.S. Pat. No. 6,995,364, incorporated by reference herein in its entirety. Use of orbitrap analyzers has been reported for qualitative and quantitative analyses of various analytes. See, e.g., U.S. Patent Application Pub. No. 2008/0118932 (filed Nov. 9, 2007); Bredehöft, et al., Rapid Commun. Mass Spectrom., 2008, 22:477-485; Le Breton, et al., Rapid Commun. Mass Spectrom., 2008, 22:3130-36; Thevis, et al., Mass Spectrom. Reviews, 2008, 27:35-50; Thomas, et al., J. Mass Spectrom., 2008, 43:908-15; Schenk, et al., BMC Medical Genomics, 2008, 1:41; and Olsen, et al., Nature Methods, 2007, 4:709-12.

As used herein, the term "operating in negative ion mode" refers to those mass spectrometry methods where negative ions are generated and detected. The term "operating in positive ion mode" as used herein, refers to those mass spectrometry methods where positive ions are generated and detected. In preferred embodiments, mass spectrometry is conducted in positive ion mode.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photoionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the ionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., Anal. Chem. 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

BRIEF DESCRIPTION OF THE DRAWINGS

FIGS. 2A-D show potential deviation of instrument response from the true m/z of the ion investigated for a theoretical peak at m/z of 1093.52094 at a mass accuracy of 120 ppm (FIG. 2A), a mass accuracy of 50 ppm (FIG. 2B), a mass accuracy of 20 ppm (FIG. 2C), and at a mass accuracy of 10 ppm (FIG. 2D).

FIG. 5A shows an exemplary high resolution/high accuracy spectrum across a m/z range of about 1154 to 1177 for human insulin generated with an QTOF mass spectrometer.

FIG. 5B shows an expanded view of the m/z range of about 1159 to 1166. Details are discussed in Example 4.

DETAILED DESCRIPTION OF THE INVENTION

Figure 1A:
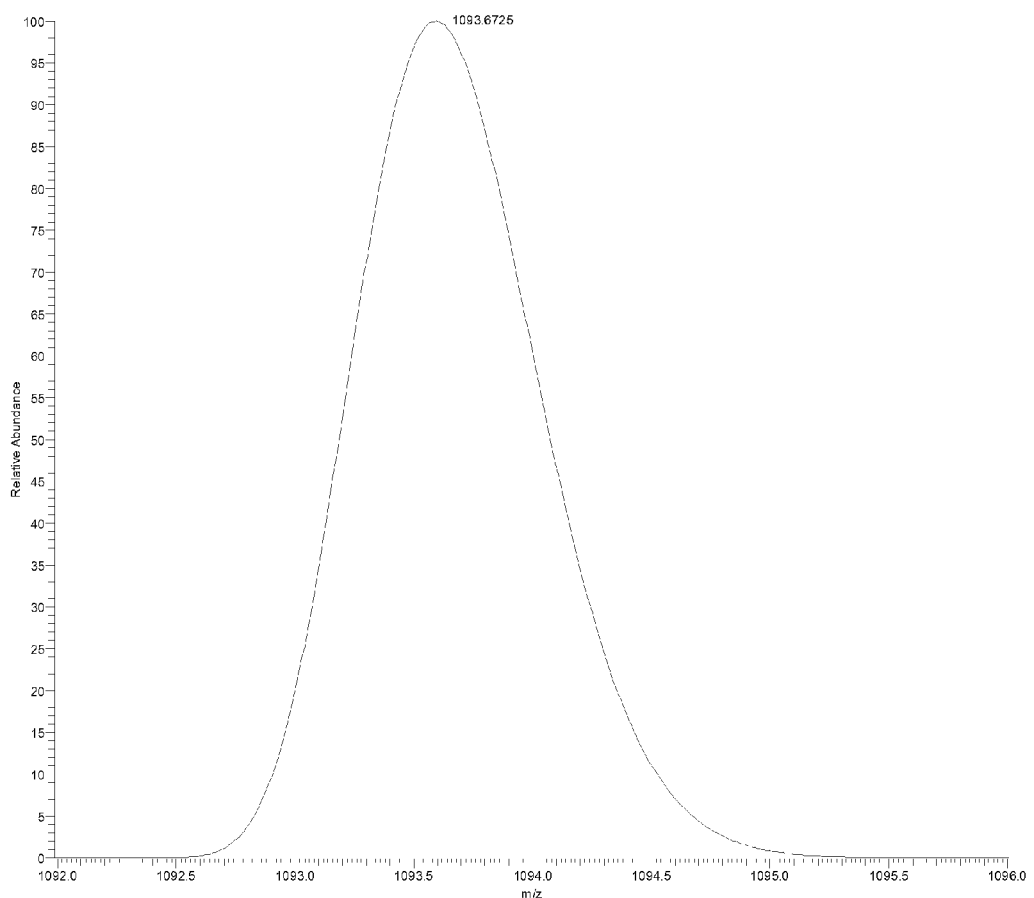
FIGS. 1A-C show theoretical mass spectra of an ion with a m/z of about 1093 as analyzed by a mass analyzer with resolving power of about 3000 (FIG. 1A), about 10,000 (FIG. 1B), and about 12,000 (FIG. 1C).
Figure 1B:
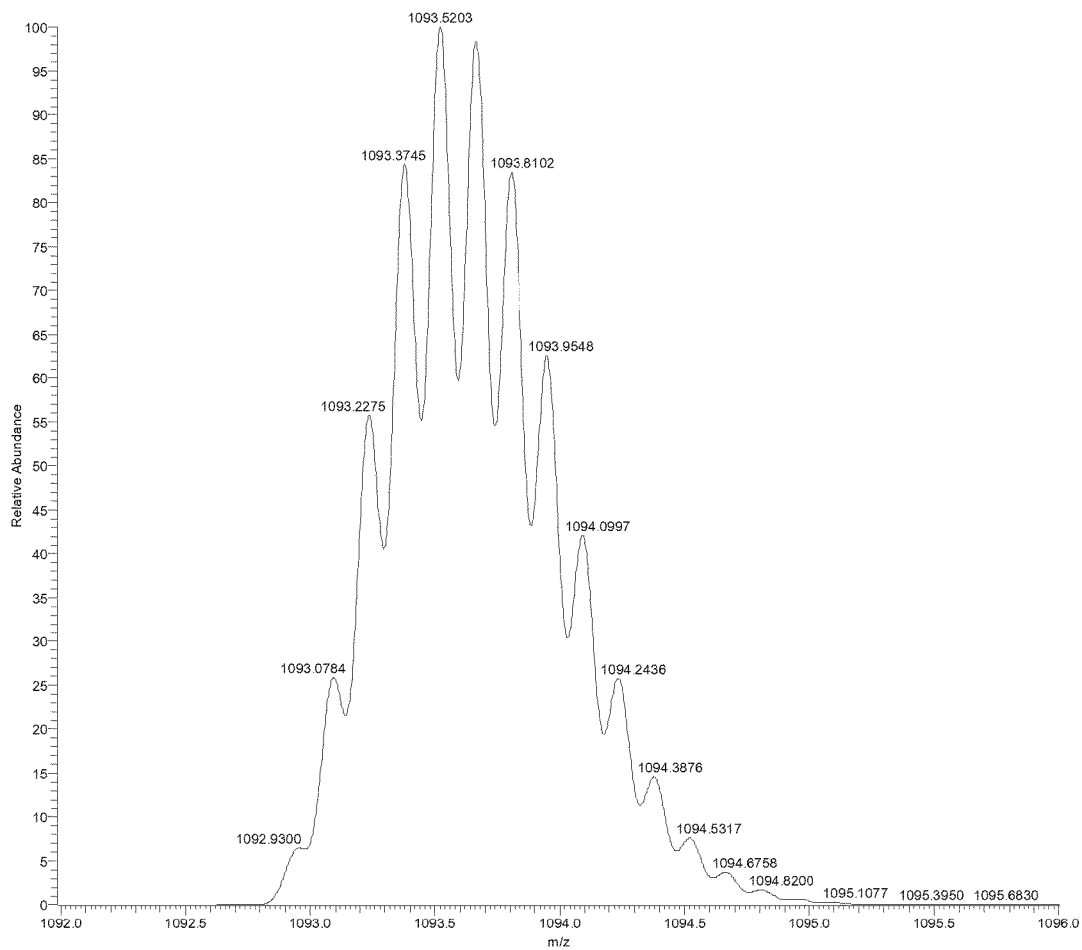
Figure 1C:
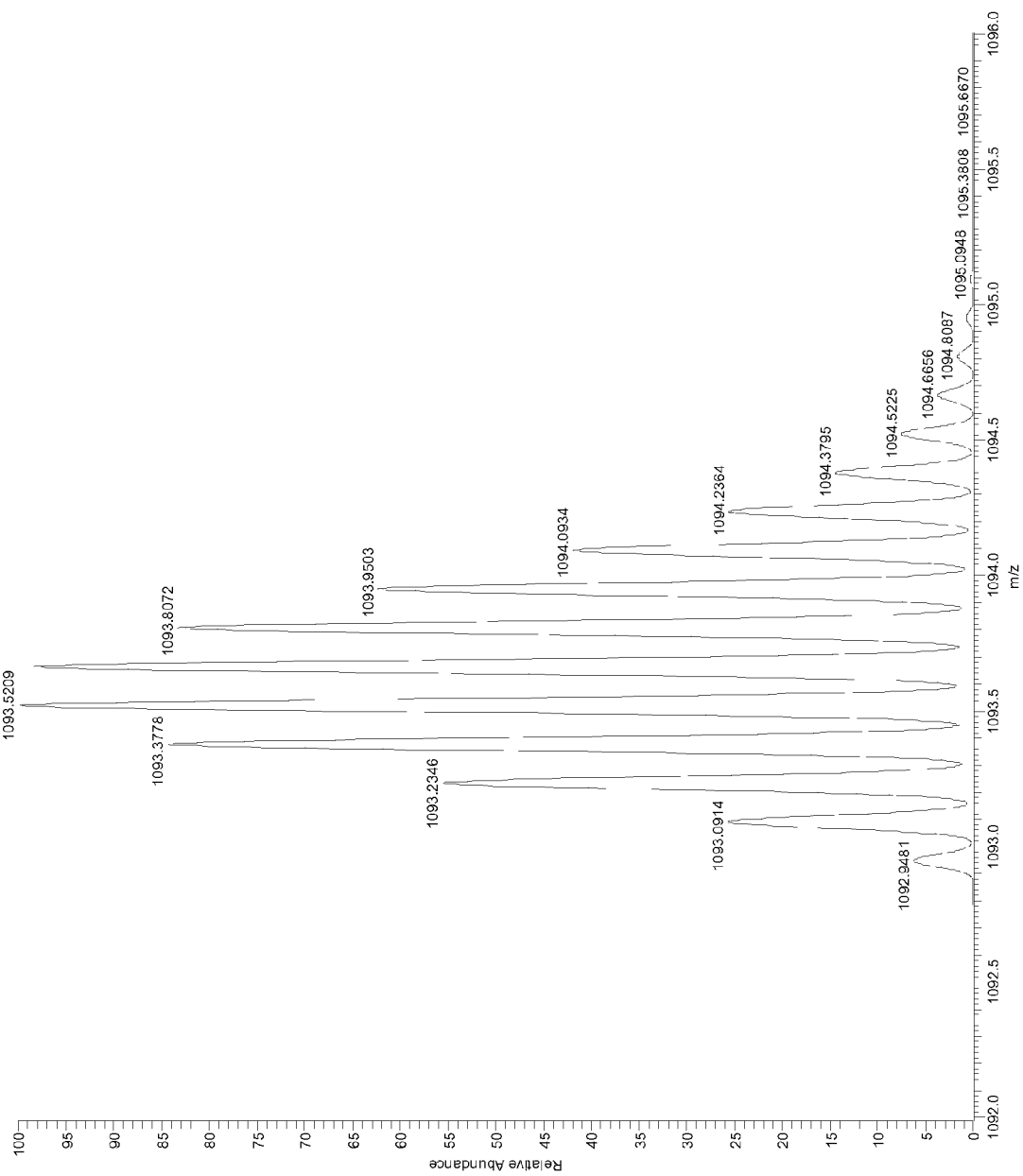

Methods are described for determining the amount of insulin in a sample. More specifically, mass spectrometric methods are described for detecting and quantifying insulin in a sample. The methods may utilize solid phase extraction (SPE) and/or liquid chromatography (LC), to perform a purification of selected analytes, combined with methods of mass spectrometry (MS), thereby providing an assay system for detecting and quantifying insulin in a sample. The preferred embodiments are particularly well suited for application in large clinical laboratories for automated insulin quantification assay.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma and serum. Such samples may be obtained, for example, from a patient; that is, a living person, male or female, presenting oneself in a clinical setting for diagnosis, prognosis, or treatment of a disease or condition. In embodiments where the sample comprises a biological sample, the methods may be used to determine the amount of insulin in the sample when the sample was obtained from the biological source.

The present invention also contemplates kits for an insulin quantitation assay. A kit for an insulin quantitation assay may include a kit comprising the compositions provided herein. For example, a kit may include packaging material and measured amounts of an isotopically labeled internal standard, in amounts sufficient for at least one assay. Typically, the kits will also include instructions recorded in a tangible form (e.g., contained on paper or an electronic medium) for using the packaged reagents for use in an insulin quantitation assay.

Calibration and QC pools for use in embodiments of the present invention are preferably prepared using a matrix similar to the intended sample matrix, provided that insulin is essentially absent.

Sample Preparation for Mass Spectrometric Analysis

In preparation for mass spectrometric analysis, insulin may be enriched relative to one or more other components in the sample by various methods known in the art, including for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

One method of sample purification that may be used prior to mass spectrometry is applying a sample to a solid-phase extraction (SPE) column under conditions where the analyte of interest is reversibly retained by the column packing material, while one or more other materials are not retained. In this technique, a first mobile phase condition can be employed where the analyte of interest is retained by the column, and a second mobile phase condition can subsequently be employed to remove retained material from the column, once the non-retained materials are washed through.

In some embodiments, insulin in a sample may be reversibly retained on a SPE column with a packing material comprising an alkyl bonded surface. For example, in some embodiments, a C-8 on-line SPE column (such as an Oasis HLB on-line SPE column/cartridge (2.1 mm×20 mm) from Phenomenex, Inc. or equivalent) may be used to enrich insulin prior to mass spectrometric analysis. In some embodiments, use of an SPE column is conducted with HPLC Grade 0.2% aqueous formic acid as a wash solution, and use of 0.2% formic acid in acetonitrile as an elution solution.

In some embodiments, insulin is not purified by any immunoaffinity technique. Some of these embodiments utilize a SPE column. In these embodiments, the SPE column is not an immunoaffinity column.

In other embodiments, the methods include immunopurifying insulin prior to mass spectrometry analysis. The immunopurification step may be performed using any of the immunopurification methods well known in the art. Often the immunopurification procedure utilizes antibodies bound, conjugated, immobilized or otherwise attached to a solid support, for example a column, well, tube, capsule, particle or the like. Generally, immunopurification methods involve (1) incubating a sample containing the analyte of interest with antibodies such that the analyte binds to the antibodies, (2) performing one or more washing steps, and (3) eluting the analyte from the antibodies.

In certain embodiments the incubation step of the immunopurification is performed with the antibodies free in solution and the antibodies are subsequently bound or attached to a solid surface prior to the washing steps. In certain embodiments this can be achieved using a primary antibody that is an anti-insulin antibody and a secondary antibody attached to a solid surface that has an affinity to the primary anti-insulin antibody. In alternative embodiments, the primary antibody is bound to the solid surface prior to the incubation step.

Appropriate solid supports include without limitation tubes, slides, columns, beads, capsules, particles, gels, and the like. In some preferred embodiments, the solid support is a multi-well plate, such as, for example, a 96 well plate, a 384-well plate or the like. In some embodiments the solid support are sepharose or agarose beads or gels. There are numerous methods well known in the art by which antibodies (for example, an insulin antibody or a secondary antibody) may be bound, attached, immobilized or coupled to a solid support, e.g., covalent or non-covalent linkages adsorption, affinity binding, ionic linkages and the like. In some embodiments antibodies are coupled using CNBr, for example the antibodies may be coupled to CNBr activated sepharose. In other embodiments, the antibody is attached to the solid support through an antibody binding protein such as protein A, protein G, protein A/G, or protein L.

The washing step of the immunopurification methods generally involve washing the solid support such that the insulin remain bound to the anti-insulin antibodies on the solid support. The elution step of the immunopurification generally involves the addition of a solution that disrupts the binding of insulin to the anti-insulin antibodies. Exemplary elution solutions include organic solutions, salt solutions, and high or low pH solutions.

Another method of sample purification that may be used prior to mass spectrometry is liquid chromatography (LC). In liquid chromatography techniques, an analyte may be purified by applying a sample to a chromatographic analytical column under mobile phase conditions where the analyte of interest elutes at a differential rate in comparison to one or more other materials. Such procedures may enrich the amount of one or more analytes of interest relative to one or more other components of the sample.

Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a partition process and may select LC, including HPLC, instruments and columns that are suitable for use with C peptide. The chromatographic analytical column typically includes a medium (i.e., a packing material) to facilitate separation of chemical moieties (i.e., fractionation). The medium may include minute particles. The particles typically include a bonded surface that interacts with the various chemical moieties to facilitate separation of the chemical moieties. One suitable bonded surface is a hydrophobic bonded surface such as an alkyl bonded or a cyano bonded surface. Alkyl bonded surfaces may include C-4, C-8, C-12, or C-18 bonded alkyl groups. In some embodiments, the chromatographic analytical column is a monolithic C-18 column. The chromatographic analytical column includes an inlet port for receiving a sample and an outlet port for discharging an effluent that includes the fractionated sample. The sample may be supplied to the inlet port directly, or from a SPE column, such as an on-line SPE column or a TFLC column. In some embodiments, an on-line filter may be used ahead of the SPE column and or HPLC column to remove particulates and phospholipids in the samples prior to the samples reaching the SPE and/or TFLC and/or HPLC columns.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In some embodiments, insulin in a sample is enriched with HPLC. This HPLC may be conducted with a monolithic C-18 column chromatographic system, for example, an Onyx Monolithic C-18 column from Phenomenex Inc. (50× 2.0 mm), or equivalent. In certain embodiments, HPLC is performed using HPLC Grade 0.2% aqueous formic acid as solvent A, and 0.2% formic acid in acetonitrile as solvent B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of insulin prior to mass spectrometry. In such embodiments, samples may be extracted using a TFLC column which captures the analyte. The analyte is then eluted and transferred on-line to an analytical HPLC column. For example, sample extraction may be accomplished with a TFLC extraction cartridge with a large particle size (50 μm) packing. Sample eluted off of this column may then be transferred on-line to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

In some embodiments, one or more of the above purification techniques may be used in parallel for purification of insulin to allow for simultaneous processing of multiple samples. In some embodiments, the purification techniques employed exclude immunopurification techniques, such as immunoaffinity chromatography.

Detection and Quantitation of Insulin by Mass Spectrometry

Mass spectrometry is performed using a mass spectrometer, which includes an ion source for ionizing the fractionated sample and creating charged molecules for further analysis. In various embodiments, insulin may be ionized by any method known to the skilled artisan. For example, ionization of insulin may be performed by electron ionization, chemical ionization, electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc. insulin may be ionized in positive or negative mode. In preferred embodiments, insulin is ionized by ESI in positive ion mode.

In mass spectrometry techniques generally, after the sample has been ionized, the positively or negatively charged ions thereby created may be analyzed to determine a mass to charge ratio (m/z). Various analyzers for determining m/z include quadrupole analyzers, ion traps analyzers, time-of-flight analyzers, Fourier transform ion cyclotron resonance mass analyzers, and orbitrap analyzers. Some exemplary ion trap methods are described in Bartolucci, et al., *Rapid Commun. Mass Spectrum.* 2000, 14:967-73.

The ions may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). In some embodiments, the mass-to-charge ratio is determined using a quadrupole analyzer. In a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of insulin. The relative abundance of a given ion may be converted into an absolute amount of the original analyte using calibration standard curves based on peaks of one or more ions of an internal or external molecular standard.

One may enhance the resolution of MS techniques employing certain mass spectrometric analyzers through "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples. In certain embodiments, a mass spectrometric instrument with multiple quadrupole analyzers (such as a triple quadrupole instrument) is employed to conduct tandem mass spectrometric analysis.

In certain embodiments using a MS/MS technique, precursor ions are isolated for further fragmentation, and collision activated dissociation (CAD) is used to generate fragment ions from the precursor ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some embodiments, insulin in a sample is detected and/or quantified using MS/MS as follows. Insulin is enriched in a sample by first subjecting the sample to SPE, then to liquid chromatography, preferably HPLC; the flow of liquid solvent from a chromatographic analytical column enters the heated nebulizer interface of an MS/MS analyzer; and the solvent/analyte mixture is converted to vapor in the heated charged tubing of the interface. During these processes, the analyte (i.e., insulin) is ionized. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the m/z of an insulin ion. Precursor ions with the correct m/z are allowed to pass into the collision chamber (Q2), while unwanted ions with any other m/z collide with the sides of the quadrupole and are eliminated. Precursor ions entering Q2 collide with neutral gas molecules (such as Argon molecules) and fragment. The fragment ions generated are passed into quadrupole 3 (Q3), where the fragment ions are selected for detection.

Ionization of insulin may result in multiply charged precursor ions (such as precursor ions of 4+, 5+, 6+, etc.). Ionization conditions, particularly the pH of the buffer utilized in electrospray techniques, greatly influence the identity and quantity of insulin precursor ions generated. For example, under acidic conditions, positive electrospray ionization may predominately generate 5+ and 6+ charged insulin precursor ions with m/z of 1162.5±0.5 and 968.5±0.5, respectively. However, under basic conditions, positive electrospray ionization may predominately generate 4+ and 5+ charged insulin precursor ions with m/z of 1453.75±0.5 and 1162.94±0.5, respectively. The methods may utilize either acidic or basic conditions; preferably acidic conditions.

The methods may involve MS/MS performed in either positive or negative ion mode; preferably positive ion mode. In certain embodiments, the electrospray buffer is acidic and Q1 selects for insulin precursor ions with an m/z of about 1162.5±0.5 or 968.5±0.5. Fragmentation of either of these insulin precursor ions generates fragment ions with m/z of about 226.21±0.5, and/or 135.6±0.5. Thus, in embodiments where Q1 selects for one or more insulin precursor ions selected from the group consisting of ions with m/z of about 1162.5±0.5 and 968.5±0.5, Q3 may select one or more fragment ions selected from the group of ions with m/z of about 226.21±0.5, and 135.6±0.5. In certain embodiments, the relative abundance of a single fragment ion from a single precursor ion may be measured. Alternatively, the relative abundances of two or more fragment ions from a single precursor ion may be measured. In these embodiments, the relative abundances of each fragment ion may be subjected to any known mathematical treatment to quantitatively assess insulin originally in the sample. In other embodiments, one or more fragment ions from two or more precursor ions may be measured and utilized as above to qualitatively assess insulin originally in the sample.

Alternate modes of operating a tandem mass spectrometric instrument that may be used in certain embodiments include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

In other embodiments, a high resolution/high accuracy mass analyzer may be used for quantitative analysis of insulin according to methods of the present invention. To achieve acceptable precision for quantitative results, the mass spectrometer must be capable of exhibiting a resolving power (FWHM) of 10,000 or more, with accuracy of about 50 ppm or less for the ions of interest; preferably the mass spectrometer exhibits a resolving power (FWHM) of 18,000 or better, with accuracy of about 5 ppm or less; such as a resolving power (FWHM) of 20,000 or better and accuracy of about 3 ppm or less; such as a resolving power (FWHM) of 25,000 or better and accuracy of about 3 ppm or less. Three exemplary analyzers capable of exhibiting the requisite level of performance for insulin ions are orbitrap mass analyzers, certain TOF mass analyzers, and Fourier transform ion cyclotron resonance mass analyzers.

Elements found in biological active molecules, such as carbon, oxygen, and nitrogen, naturally exist in a number of different isotopic forms. For example, most carbon is present as $^{12}C$, but approximately 1% of all naturally occurring carbon is present as $^{13}C$. Thus, some fraction of naturally occurring molecules containing at least one carbon atom will contain at least one $^{13}C$ atom. Inclusion of naturally occurring elemental isotopes in molecules gives rise to multiple molecular isotopic forms. The difference in masses of molecular isotopic forms is at least 1 atomic mass unit (amu). This is because elemental isotopes differ by at least one neutron (mass of one neutron≈1 amu). When molecular isotopic forms are ionized to multiply charged states, the mass distinction between the isotopic forms can become difficult to discern because mass spectrometric detection is based on the mass to charge ratio (m/z). For example, two isotopic forms differing in mass by 1 amu that are both ionized to a 5+ state will exhibit differences in their m/z of only 0.2. High resolution/high accuracy mass spectrometers are capable of discerning between isotopic forms of highly multiply charged ions (such as ions with charges of ±2, ±3, +4, ±5, or higher).

Figure 4:
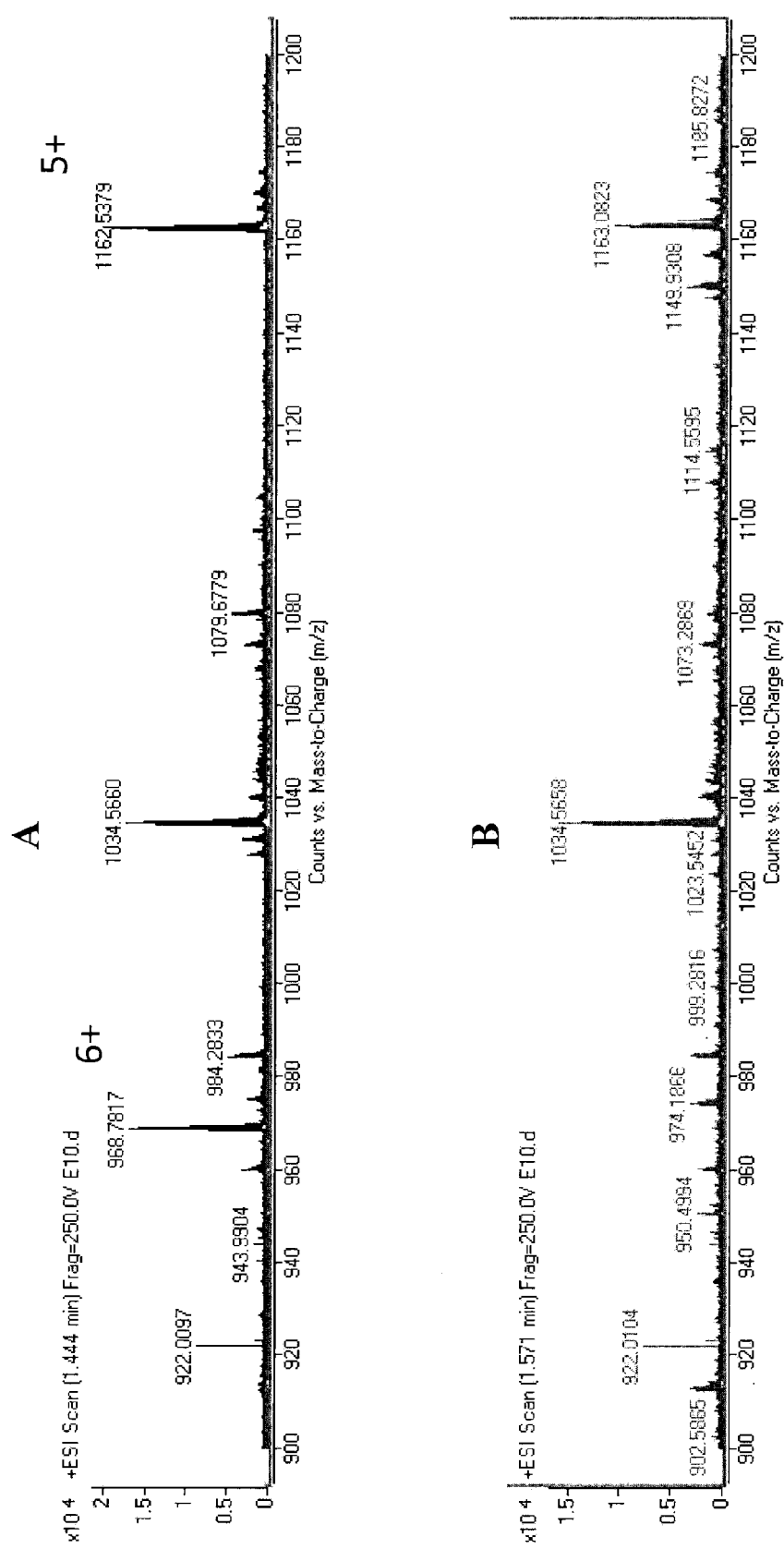
FIG. 4A shows an exemplary spectrum across a m/z range of about 900 to 1200 for human insulin generated with an QTOF mass spectrometer.
FIG. 4B shows contaminant peaks from strip serum sample matrix generated with an QTOF mass spectrometer. Details are discussed in Example 4.
Figure 6:
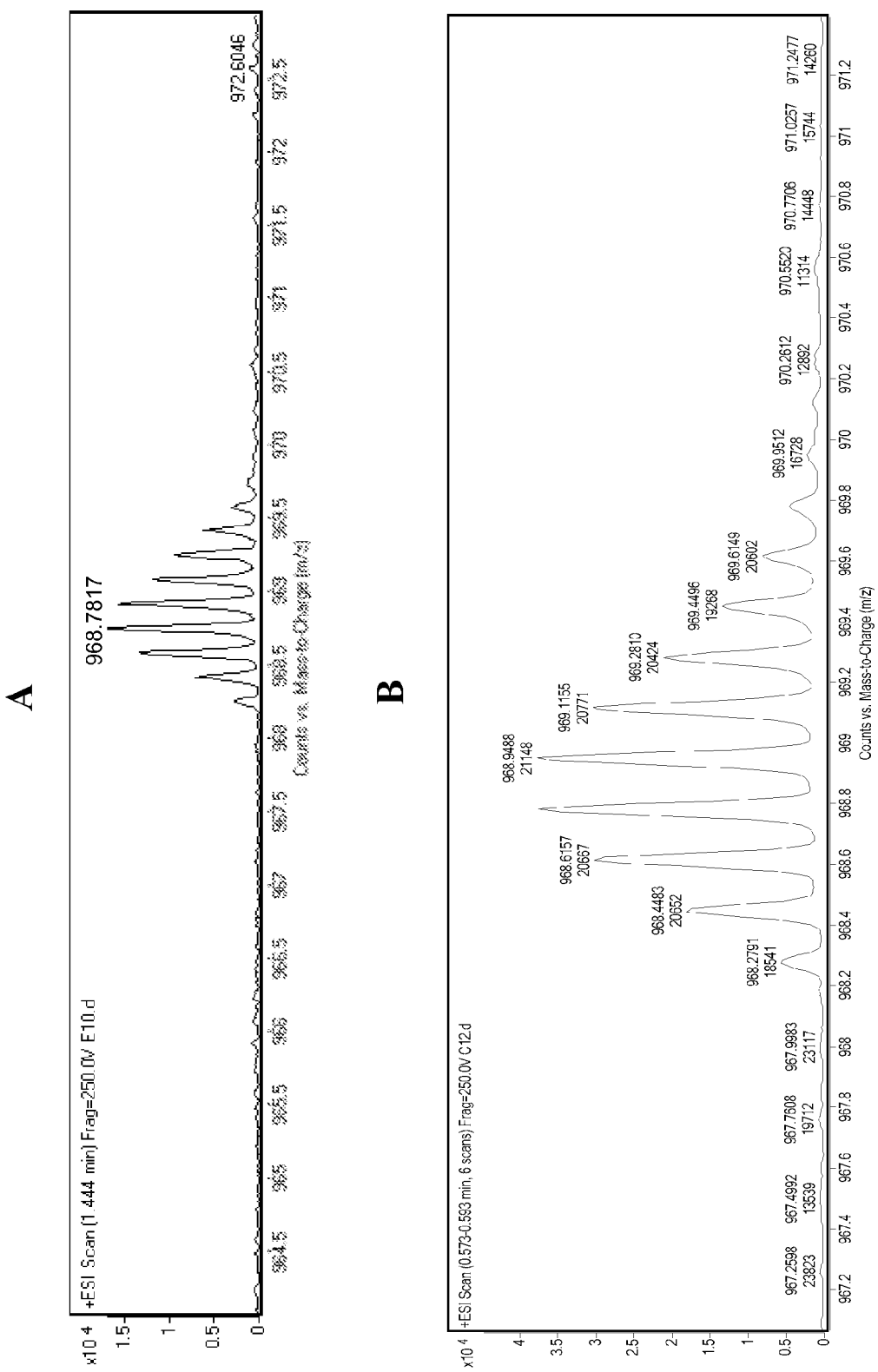
FIG. 6A shows an exemplary high resolution/high accuracy spectrum across a m/z range of about 964 to 973 for human insulin generated with an QTOF mass spectrometer.
FIG. 6B shows an expanded view of the m/z range of about 967 to 971. Details are discussed in Example 4.

Due to naturally occurring elemental isotopes, multiple isotopic forms typically exist for every molecular ion (each of which may give rise to a separately detectable spectrometric peak if analyzed with a sensitive enough mass spectrometric instrument). The m/z ratios and relative abundances of multiple isotopic forms collectively comprise an isotopic signature for a molecular ion. In some embodiments, the m/z ratios and relative abundances for two or more molecular isotopic forms may be utilized to confirm the identity of a molecular ion under investigation. In some embodiments, the mass spectrometric peak from one or more isotopic forms is used to quantitate a molecular ion. In some related embodiments, a single mass spectrometric peak from one isotopic form is used to quantitate a molecular ion. In other related embodiments, a plurality of isotopic peaks are used to quantitate a molecular ion. In these later embodiments, the plurality of isotopic peaks may be subject to any appropriate mathematical treatment. Several mathematical treatments are known in the art and include, but are not limited to summing the area under multiple peaks, or averaging the response from multiple peaks. Exemplary spectra demonstrating multiple isotopic forms of 5+ and 6+ insulin ions are seen in FIGS. 4-6. As seen in FIG. 5A-B, peaks from various isotopic forms of the 5+ insulin ion are seen at about 1161.72, 1161.92, 1162.12, 1162.32, 1162.52, 1162.72, 1162.92, 1163.12, and 1163.32. As seen in FIG. 6A-B, peaks from various isotopic forms of the 6+ insulin ion are seen at about 968.28, 968.45, 968.62, 968.79, 968.95, 969.12, 969.28, 968.45, and 969.61. Note, however, that the precise masses observed for isotopic variants of any ion may vary slightly because of instrumental variance.

In some embodiments, the relative abundance of one or more ion is measured with a high resolution/high accuracy mass spectrometer in order to qualitatively assess the amount of insulin in the sample. In some embodiments, the one or more ions measured by high resolution/high accuracy mass spectrometry are multiply charged insulin ions. These multiply charged ions may include one or more of ions with a m/z within the ranges of about 1453±0.8 (i.e., one or more monoisotopic peaks from a 4+ ion), and/or 1162±1 (i.e., one or more monoisotopic peaks from a 5+ ion), and/or about 968.8±1.5 (i.e., one or more monoisotopic peaks from a 6+ ion).

Use of high resolution orbitrap analyzers has been reported for qualitative and quantitative analyses of various analytes. See, e.g., U.S. Patent Application Pub. No. 2008/0118932 (filed Nov. 9, 2007); Bredehoft, et al., Rapid Commun. Mass Spectrom., 2008, 22:477-485; Le Breton, et al., Rapid Commun. Mass Spectrom., 2008, 22:3130-36; Thevis, et al., Mass Spectrom. Reviews, 2008, 27:35-50; Thomas, et al., J. Mass Spectrom., 2008, 43:908-15; Schenk, et al., BMC Medical Genomics, 2008, 1:41; and Olsen, et al., Nature Methods, 2007, 4:709-12.

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of insulin. Methods of generating and using such standard curves are well known in the art and one of ordinary skill is capable of selecting an appropriate internal standard. For example, in preferred embodiments one or more forms of isotopically labeled insulin may be used as internal standards. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium ($^2$H), $^{13}$C, and $^{15}$N. One or more isotopic labels can be incorporated at one or more positions in the molecule and one or more kinds of isotopic labels can be used on the same isotopically labeled molecule.

Quantitation of Insulin by Quantitation of Unmodified Insulin A and/or B Chain by Mass Spectrometry In other embodiments, insulin may be subjected to a chemical treatment to generate insulin's constituent chains prior to mass spectrometric analysis. Insulin's A-chain and B-chain may be separated by any chemical treatment known in the art to cause disulfide reduction. For example, insulin may be treated with TCEP (tris(2-carboxyethyl)phosphine to reduce insulin's disulfide bridges and separate the A chain and B chain.

The A-chains and B-chains may then be subject to any one or more of the purification steps described above for purification of insulin. In preferred embodiments, A-chains and/or B-chains are subject to purification by HPLC prior to mass spectrometric analysis.

Once purified, A-chains and/or B-chains are then subjected to an ionization source. As with insulin, the skilled artisan will understand that the choice of ionization method may be determined based on the analyte to be measured, type of sample, the type of detector, the choice of positive versus negative mode, etc. Insulin A-chains and B-chains may be ionized in positive or negative mode. In preferred embodiments, insulin A-chains and/or B-chains are ionized by ESI in positive mode.

Ionization of insulin A-chains may result in multiply charged A-chain precursor ions (such as precursor ions of 2+, 3+, etc.). For example, positive electrospray ionization of insulin A-chain molecules may generate 2+ and 3+ charged A-chain precursor ions with m/z of 1192.0±0.5 and 795.0±0.5, respectively. Similar to insulin, the identity and quantity of the multiply charged species generated from ionization of insulin A-chains is affected by the ionization conditions employed. In preferred embodiments, insulin A-chains are ionized under acidic conditions.

In embodiments where insulin A-chains are subject to tandem mass spectrometric analysis, Q1 may select for one or more insulin A-chain precursor ions with an m/z of about 1192.0±0.5 and 795.0±0.5. Fragmentation of either of these insulin A-chain precursor ions may generate fragment ions with m/z of about 513.0±0.5, 399.0±0.5, 236.0±0.5, and 133.0±0.5. Thus, in embodiments where Q1 selects for one or more insulin A-chain precursor ions selected from the group consisting of ions with m/z of about 1192.0±0.5 and 795.0±0.5, Q3 may select one or more fragment ions selected from the group of ions with m/z of about 513.0±0.5, 399.0±0.5, 236.0±0.5, and 133.0±0.5. In certain embodiments, the relative abundance of a single fragment ion from a single precursor ion may be measured. Alternatively, the relative abundances of two or more fragment ions from a single precursor ion may be measured. In these embodiments, the relative abundances of each fragment ion may be subjected to any known mathematical treatment to quantitatively assess insulin originally in the sample. In other embodiments, one or more fragment ions from two or more precursor ions may be measured and utilized as above to qualitatively assess insulin originally in the sample.

Similarly, ionization of insulin B-chains may result in multiply charged B-chain precursor ions (such as precursor ions of 3+, 4+, 5+, etc.). For example, positive electrospray ionization of insulin B-chain molecules may generate 3+, 4+, and 5+ charged B-chain precursor ions with m/z of 1144.2±0.5, 858.3±0.5, and 686.8±0.5, respectively. Similar to insulin, the identity and quantity of the multiply charged species generated from ionization of insulin B-chains is affected by the ionization conditions employed. In preferred embodiments, insulin B-chains are ionized under acidic conditions.

In embodiments where insulin B-chains are subject to tandem mass spectrometric analysis, Q1 may select for one or more insulin B-chain precursor ions with an m/z of about 1144.2±0.5, 858.3±0.5, and 686.8±0.5. Fragmentation of these three insulin B-chain precursor ions may generate fragment ions with m/z of about 825.4±0.5, 768.5±0.5, 753.2±0.5, 345.0±0.5, and 226.2±0.5. Thus, in embodiments where Q1 selects for one or more insulin B-chain precursor ions selected from the group consisting of ions with m/z of about 1144.2±0.5, 858.3±0.5, and 686.8±0.5, Q3 may select one or more fragment ions selected from the group of ions with m/z of about 825.4±0.5, 768.5±0.5, 753.2±0.5, 345.0±0.5, and 226.2±0.5; preferably selected from the group of ions with m/z of about 345.0±0.5 and 226.2±0.5. In certain embodiments, the relative abundance of a single fragment ion from a single precursor ion may be measured. Alternatively, the relative abundances of two or more fragment ions from a single precursor ion may be measured. In these embodiments, the relative abundances of each fragment ion may be subjected to any known mathematical treatment to quantitatively assess insulin originally in the sample. In other embodiments, one or more fragment ions from two or more precursor ions may be measured and utilized as above to qualitatively assess insulin originally in the sample.

Quantitation of Insulin by Quantitation of Chemically Modified Insulin A and/or B Chain by Mass Spectrometry In alternative embodiments, the separate insulin A-chains and B-chains may be subjected to one or more chemical modification steps prior to ionization and/or purification. For example, once separated, insulin A-chain and B-chain molecules may undergo carbamidomethylation to fully alkylate constituent cysteines. For example, carbamidomethylation may be achieved by subjecting insulin A-chain and/or B-chain to react with iodoacetamide after reduction with DTT (1,4-Dithiothreitol). Carbamidomethylation of an insulin A-chain results in the alkylation of 4 cysteines, causing a mass increase of about 228.08 amu (about 57.02 per cysteine). Carbamidomethylation of an insulin B-chain results in the alkylation of 2 cysteines, causing a mass increase of about 114.04 amu (about 57.02 per cysteine).

Once purified, chemically modified (e.g., alkylated) A-chains and/or B-chains are subjected to an ionization source. As with insulin, the skilled artisan will understand that the choice of ionization method may be determined based on the analyte to be measured, type of sample, the type of detector, the choice of positive versus negative mode, etc. Alkylated insulin A-chains and B-chains may be ionized in positive or negative mode. In preferred embodiments, alkylated insulin A-chains and/or B-chains are ionized by ESI in positive mode.

Ionization of alkylated insulin A-chains may result in multiply charged alkylated A-chain precursor ions (such as precursor ions of 2+, 3+, etc.). For example, positive electrospray ionization of alkylated insulin A-chain molecules may generate 2+ and 3+ charged alkylated A-chain precursor ions with m/z of 1306.0±0.5 and 871.0±0.5, respectively. Similar to insulin, the identity and quantity of the multiply charged species generated from ionization of alkylated insulin A-chains is affected by the ionization conditions employed. In preferred embodiments, alkylated insulin A-chains are ionized under acidic conditions.

In embodiments where alkylated insulin A-chains are subject to tandem mass spectrometric analysis, Q1 may select for one or more alkylated insulin A-chain precursor ions with an m/z of about 1306.0±0.5 and 871.0±0.5. Fragmentation of either of these alkylated insulin A-chain precursor ions may generate fragment ions with m/z of about 570.0±0.5, 456.0±0.5, 293.0±0.5, and 133.0±0.5. Thus, in embodiments where Q1 selects for one or more alkylated insulin A-chain precursor ions selected from the group consisting of ions with m/z of about 1192.0±0.5 and 795.0±0.5, Q3 may select one or more fragment ions selected from the group of ions with m/z of about 570.0±0.5, 456.0±0.5, 293.0±0.5, and 133.0±0.5. In certain embodiments, the relative abundance of a single fragment ion from a single precursor ion may be measured. Alternatively, the relative abundances of two or more fragment ions from a single precursor ion may be measured. In these embodiments, the relative abundances of each fragment ion may be subjected to any known mathematical treatment to quantitatively assess insulin originally in the sample. In other embodiments, one or more fragment ions from two or more precursor ions may be measured and utilized as above to qualitatively assess insulin originally in the sample.

Similarly, ionization of alkylated insulin B-chains may result in multiply charged alkylated B-chain precursor ions (such as precursor ions of 3+, 4+, 5+, etc.). For example, positive electrospray ionization of alkylated insulin B-chain molecules may generate 3+, 4+, and 5+ charged alkylated B-chain precursor ions with m/z of 1181.9±0.5, 886.9±0.5, and 709.8±0.5, respectively. Similar to insulin, the identity and quantity of the multiply charged species generated from ionization of alkylated insulin B-chains is affected by the ionization conditions employed. In preferred embodiments, alkylated insulin B-chains are ionized under acidic conditions.

In embodiments where alkylated insulin B-chains are subject to tandem mass spectrometric analysis, Q1 may select for one or more insulin B-chain precursor ions with an m/z of about 1181.9±0.5, 886.9±0.5, and 709.8±0.5. Fragmentation of these three alkylated insulin B-chain precursor ions may generate fragment ions with m/z of about 345.0±0.5 and 226.2±0.5. Thus, in embodiments where Q1 selects for one or more alkylated insulin B-chain precursor ions selected from the group consisting of ions with m/z of about 1144.2±0.5, 858.3±0.5, and 686.8±0.5, Q3 may select one or more fragment ions selected from the group of ions with m/z of about 345.0±0.5 and 226.2±0.5. In certain embodiments, the relative abundance of a single fragment ion from a single precursor ion may be measured. Alternatively, the relative abundances of two or more fragment ions from a single precursor ion may be measured. In these embodiments, the relative abundances of each fragment ion may be subjected to any known mathematical treatment to quantitatively assess insulin originally in the sample. In other embodiments, one or more fragment ions from two or more precursor ions may be measured and utilized as above to qualitatively assess insulin originally in the sample.

One or more steps of any of the above described methods may be performed using automated machines. In certain embodiments, one or more purification steps are performed on-line, and more preferably all of the purification and mass spectrometry steps may be performed in an on-line fashion.

The following Examples serve to illustrate the invention. These Examples are in no way intended to limit the scope of the methods.

EXAMPLES

Example 1: Sample Preparation

Mock serum samples containing various amounts of insulin were prepared by spiking human insulin in mock serum (40 mg/mL Bovine Serum Albumin (BSA) in Phosphate Buffered Saline (PBS) buffer with 0.002% protease inhibitor AEBSF) at various concentrations for assessment of linear response (discussed below in Example 4).

Human insulin was also spiked in double charcoal stripped serum obtained from Golden West Biologicals, Inc. at various concentrations to assess linearity of response (discussed below in Example 4).

Example 2: Enrichment of Insulin Prior to Mass Spectrometry

Sample injection of the above prepared human insulin-spiked mock and stripped sera was performed with a Cohesive Technologies Aria TX-420 system using Aria OS V 1.6 or newer software.

75 µL samples were introduced into a Waters Oasis HLB (25 µm, 2.1×20 mm), on-line solid phase extraction (SPE) column. The SPE column retained human insulin while letting other serum proteins and large molecules flow through.

The insulin was eluted off the extraction column with 0.2% formic acid in 40% acetonitrile and onto the analytical column (monolithic C18 analytical column from Phenomenex Inc. (5 µm particle size, 50×2.1 mm)). An HPLC gradient was applied to the analytical column, to separate insulin from other analytes contained in the sample. Mobile phase A was 0.2% formic acid in water and mobile phase B was 0.2% formic acid in acetonitrile. The HPLC gradient started with a 28.5% organic gradient which was ramped to 37% in approximately 90 seconds.

The insulin enriched samples were then subjected to high resolution/high accuracy MS or MS/MS for quantitation of insulin.

Example 3: pH Effect on Ionization of Insulin

Ionization of insulin was conducted with an ESI source in positive ion mode. While using this ionization source to generate positive insulin ions, it was observed that the pH of the electrospray carrier solution affected the quantity and identity of the insulin ions generated.

Figure 3A:
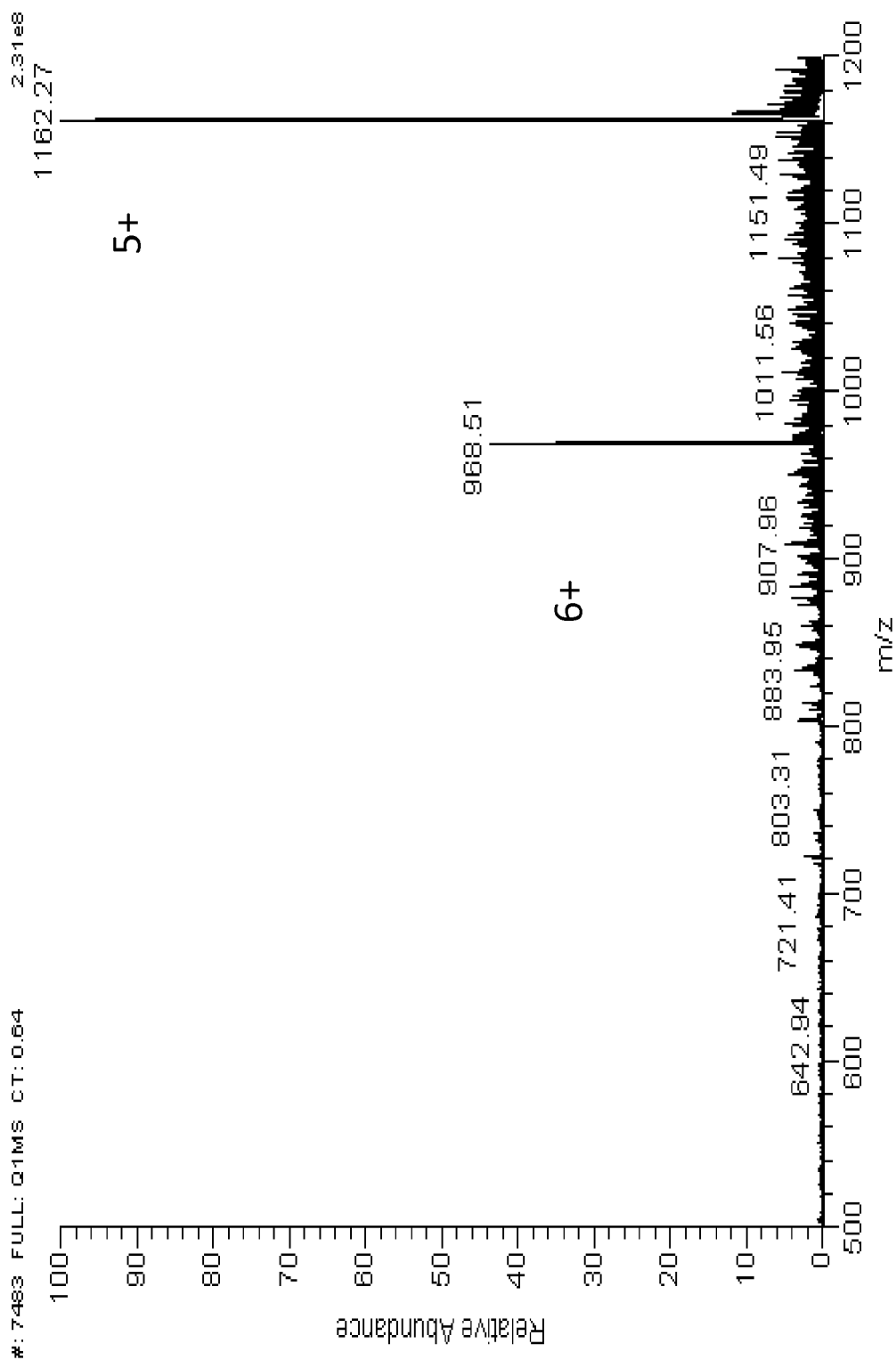
FIGS. 3A and B show exemplary spectra collected for ionization of human insulin by ESI ion positive ion mode under acidic and basic conditions, respectively. Details are described in Example 3.

Under acidic conditions, multiply charged insulin ions were observed with m/z of 968.5±0.50 (for the 6+ ion) and 1162.3±0.50 (for the 5+ ion). An exemplary spectra collected from ionization of insulin under acidic conditions is shown in FIG. 3A.

Figure 3B:
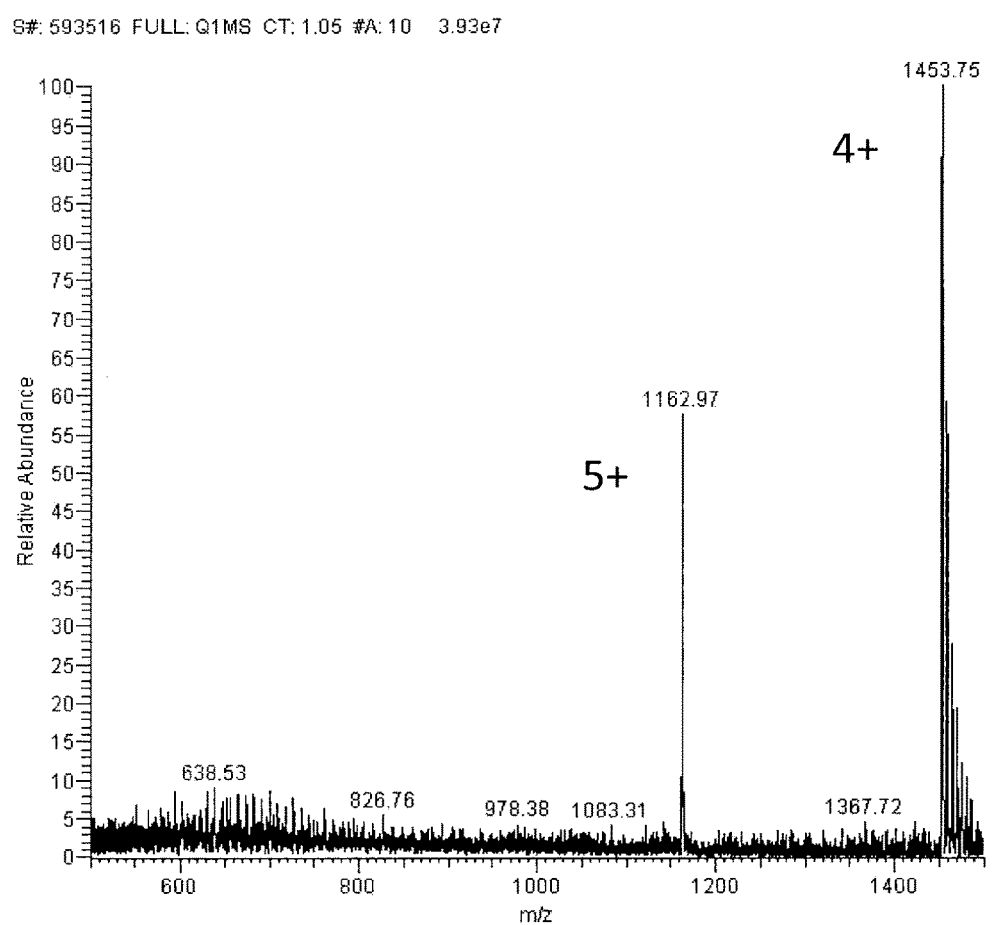

Under basic conditions, multiply charged insulin ions were observed with m/z of 1163.0±0.50 (for the 5+ ion) and 1453.8±0.50 (for the 4+ ion). An exemplary spectra collected from ionization of insulin under basic conditions is shown in FIG. 3B.

Sufficient signal was generated under both acidic and basic conditions that quantitative analysis could be conducted under either condition.

Example 4: Detection and Quantitation of Insulin by High Resolution/High Accuracy MS High resolution/high accuracy MS was performed using an Agilent TOF MS system (Agilent Technologies, Inc.). This system employs a MS analyzer capable of high resolution/high accuracy MS. The instrument exhibits resolution of approximately 25,000 FWHM, and mass accuracy of approximately 1 ppm while measuring insulin.

Ionization was conducted with an ESI source in positive ion mode. As discussed in Example 3, the pH of the electrospray carrier solution affected the quantity and identity of the insulin ions generated. As the samples prepared in Example 1 were eluted from the SPE column with a formic acid solution, the samples were acidified prior to ionization. As described in Example 3, multiply charged insulin ions were observed in the 6+ and 5+ charge states.

Contaminant peaks were observed to elute from stripped serum samples. FIG. 4A shows an exemplary spectrum across a m/z range of about 900 to 1200 for insulin in mock serum samples generated with an QTOF mass spectrometer. FIG. 4B shows contaminant peaks from strip serum sample matrix generated with an QTOF mass spectrometer. The source of the contaminant peaks was seen to elute at a different time than the insulin peaks (data not shown).

An exemplary high resolution/high accuracy spectra across the m/z range of about 1155 to 1176 showing individual isotopic peaks of the 5+ ion is seen in FIG. 5A. A close up of the portion of the spectra between about 1159 and 1166 is seen in FIG. 5B. As seen in the spectra, exemplary individual isotopic peaks are observed at m/z of about 1161.72, 1161.92, 1162.12, 1162.32, 1162.52, 1162.72, 1162.92, 1163.12, and 1163.34.

An exemplary high resolution/high accuracy spectra across the m/z range of about 964 to 973 showing individual isotopic peaks of the 6+ ion is seen in FIG. 6A. A close up of the portion of the spectra between about 967 and 971.4 is seen in FIG. 6B. As seen in the spectra, exemplary individual isotopic peaks are observed at m/z of about 968.28, 968.45, 968.62, 968.79, 968.95, 968.12, 968.28, 968.45, and 968.61.

Figure 7:
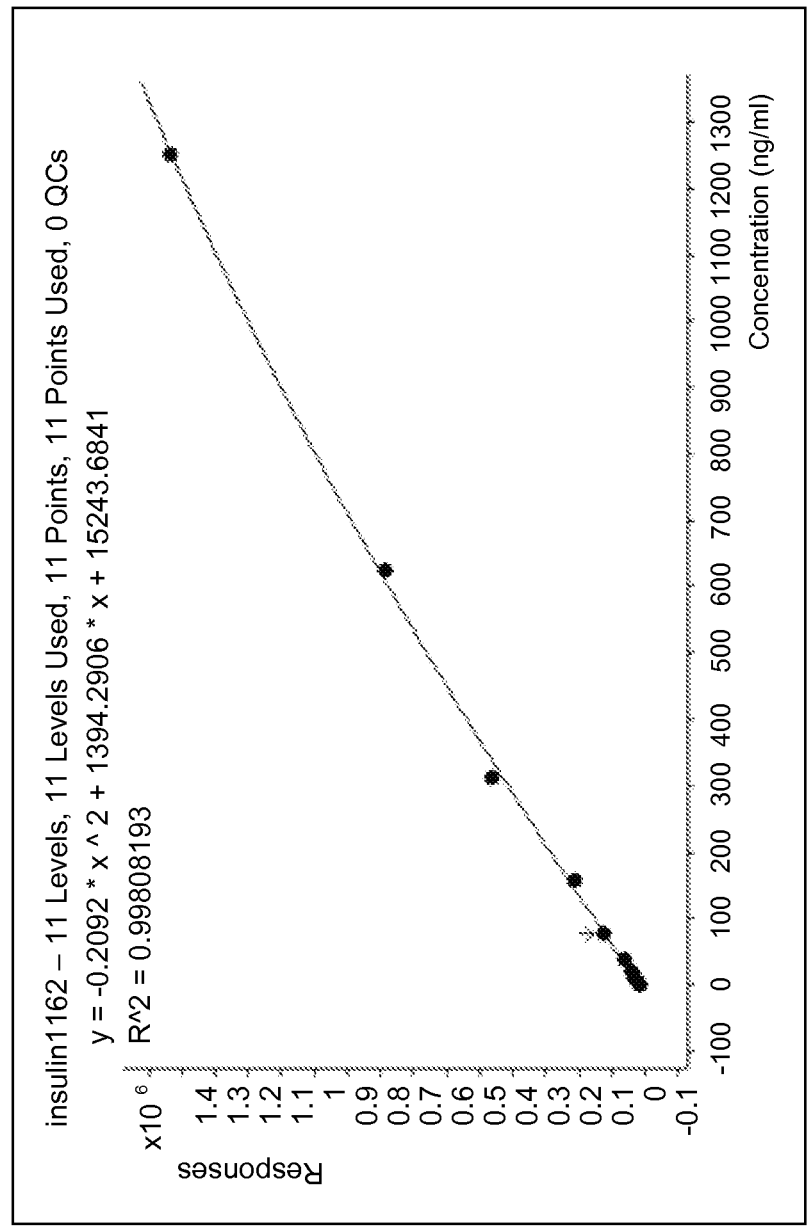
FIG. 7 shows a plot of the linearity of quantitation of human insulin in spiked mock serum standards measured with high resolution/high accuracy MS of insulin. Details are described in Example 4.
Figure 8:
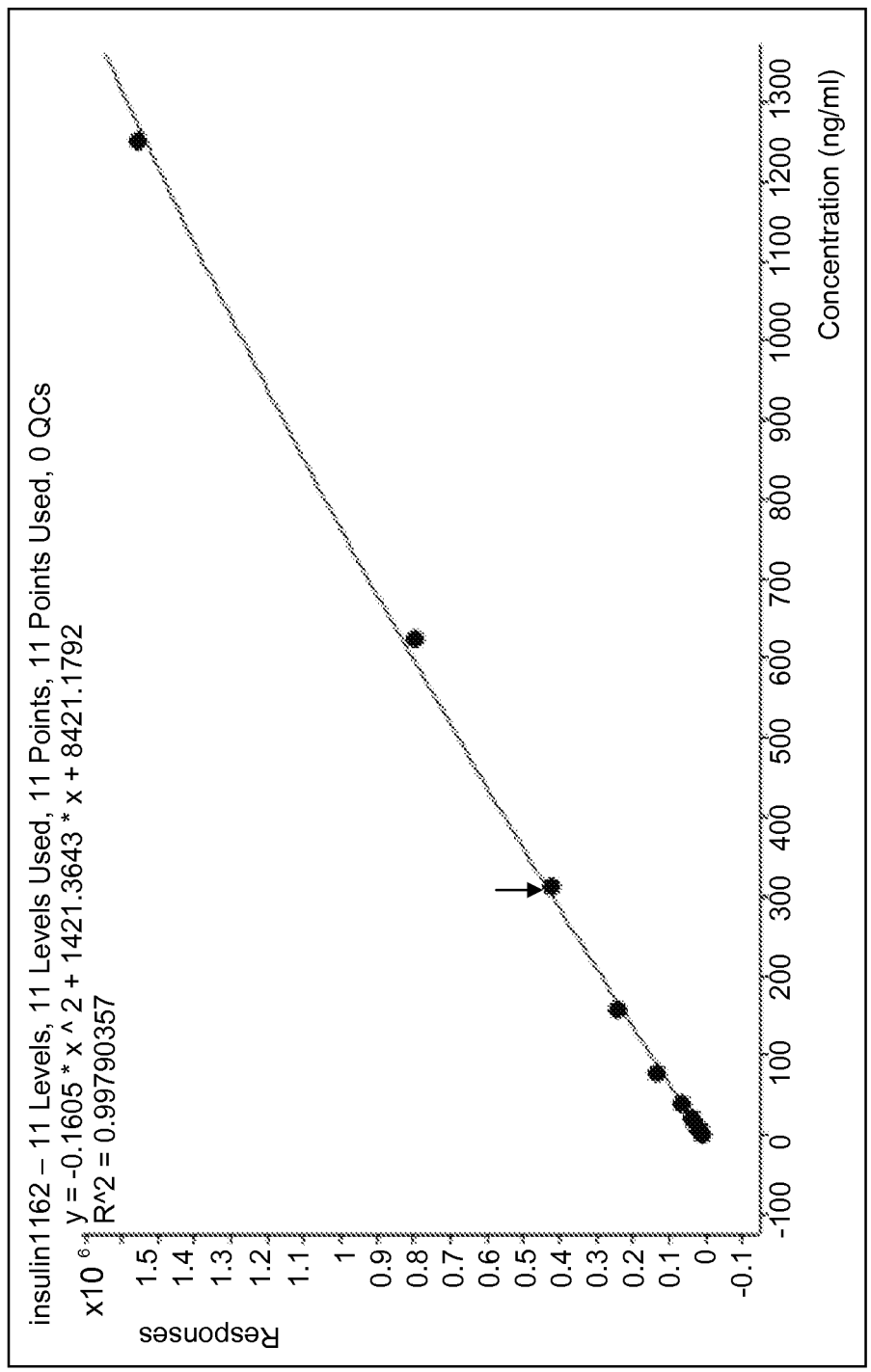
FIG. 8 shows a plot of the linearity of quantitation of human insulin in spiked stripped serum standards measured with high resolution/high accuracy MS of insulin. Details are described in Example 4.

Data was collected for the ion with m/z of 1162.54±0.10 for quantitation of insulin in spiked mock and striped serum samples to assess linearity of quantitation. Both sample types demonstrated linearity across a concentration range of about 1.22 ng/mL to 1250 ng/mL. Graphs showing the linearity of the data for insulin detection in spiked mock serum samples and spiked stripped serum samples are shown in FIGS. 7 and 8, respectively. The goodness of fits ($R^2$) for insulin by high resolution/high accuracy mass spectrometric quantitation were determined to be 0.9981 in spiked mock serum, and 0.9979 in spiked stripped serum

Example 5: Detection and Quantitation of Insulin by Tandem MS

MS/MS was performed using a Thermo TSQ Vantage MS/MS system (Thermo Electron Corporation). The following software programs, all from Thermo Electron, were used in the Examples described herein: TSQ Vantage V 2.0.0 or newer, Xcalibur V 2.0 or newer, and LCQuan V 2.5 or newer. Liquid solvent/analyte exiting the analytical column flowed to the ESI source interface of the MS/MS analyzer. The solvent/analyte mixture was converted to vapor in the heated tubing of the interface. Analytes were ionized by ESI in positive ion mode under acidic conditions.

Figure 9:
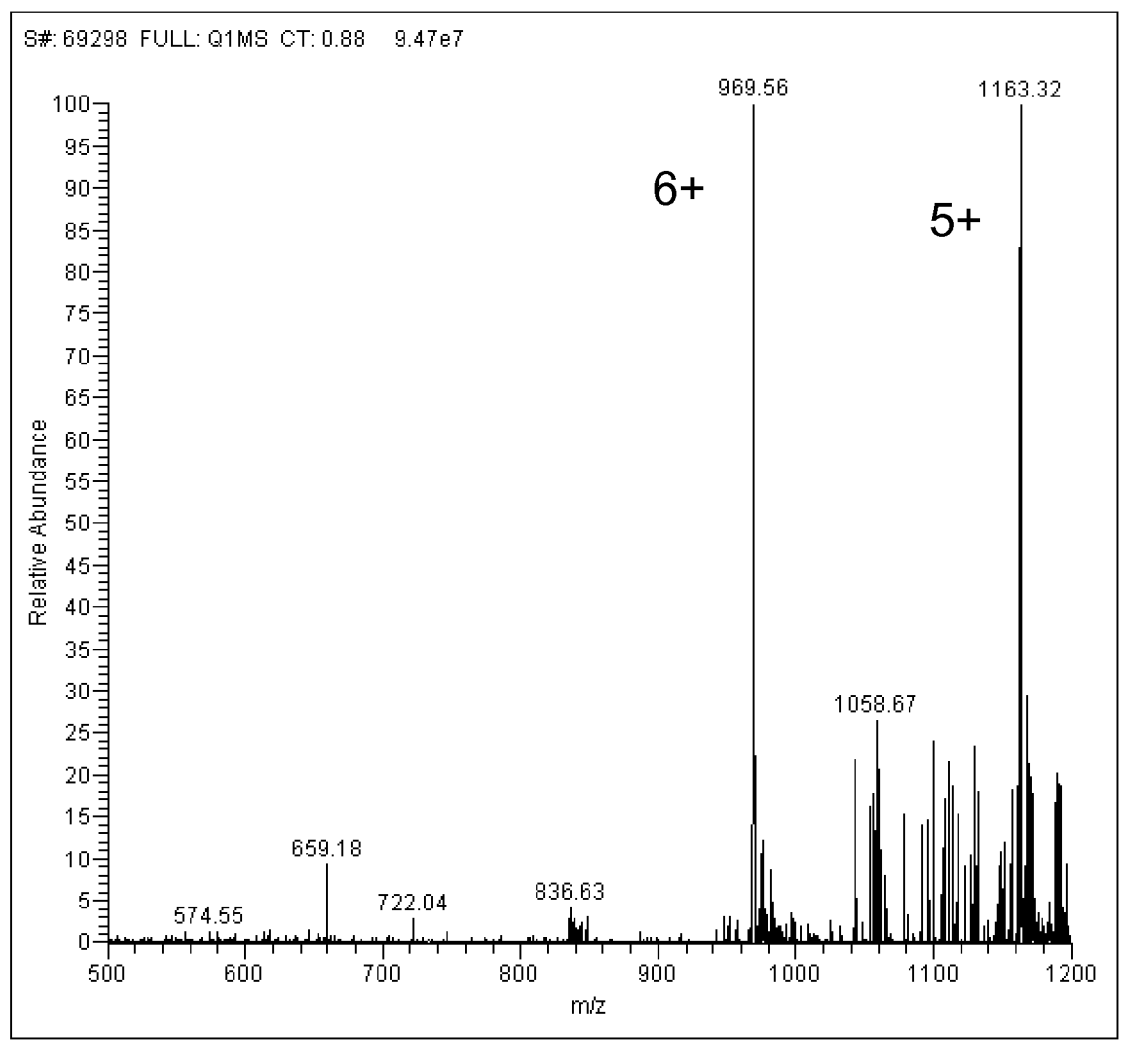
FIG. 9 shows a tandem mass spectrometry Q1 scan showing generation of human insulin precursor ions in a 5+ and 6+ charge state. Details are described in Example 5.
Figure 10:
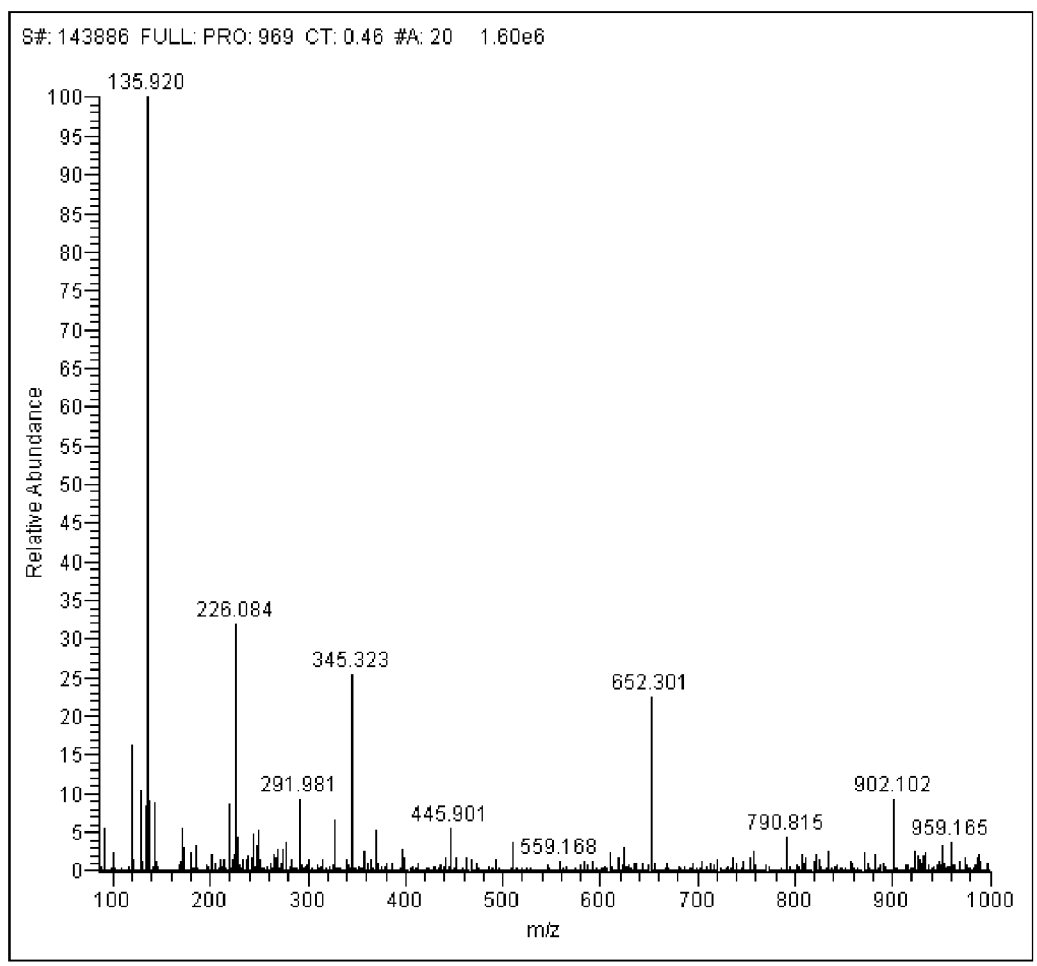
FIG. 10 shows a product ion scan from fragmentation of a human insulin precursor ion in a 6+ charge state. Details are discussed in Example 5.
Figure 11:
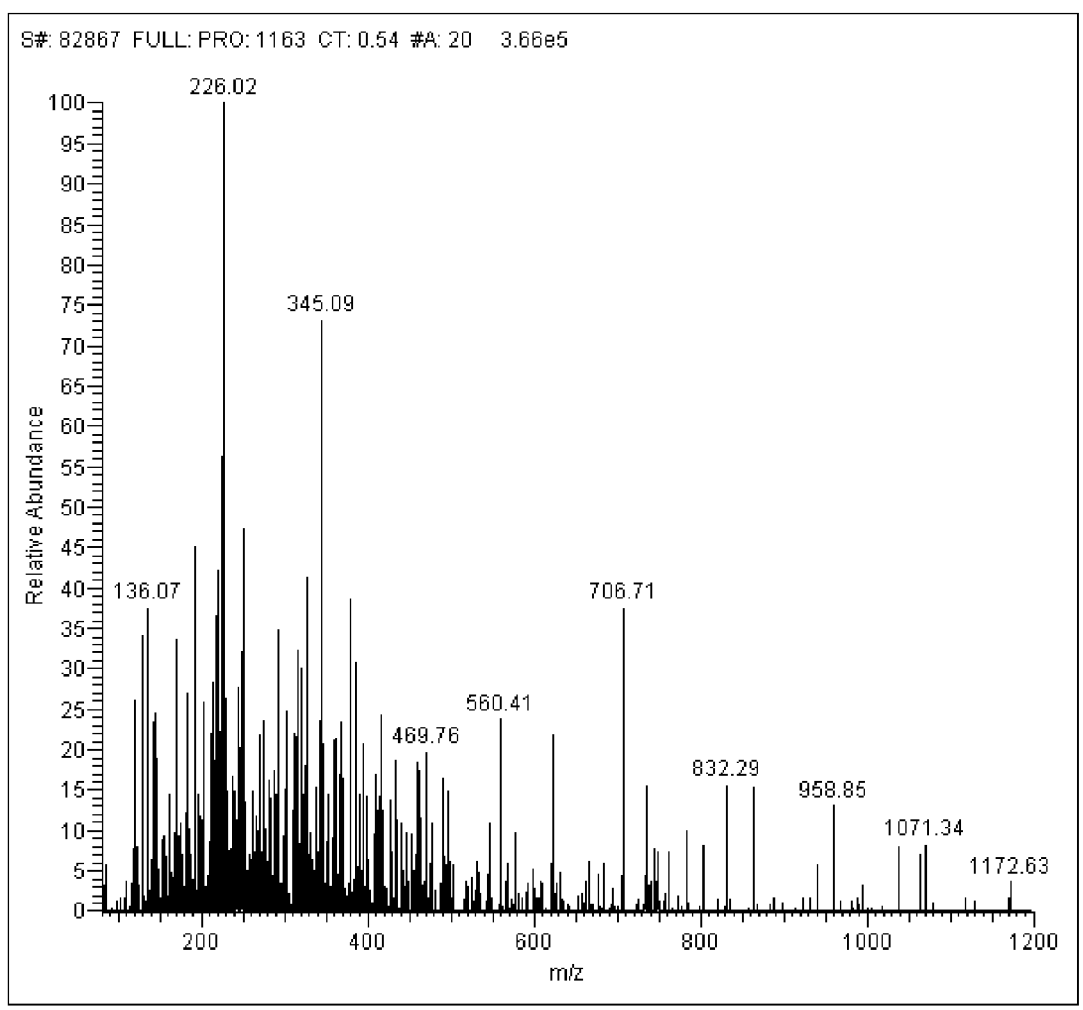
FIG. 11 shows a product ion scan from fragmentation of a human insulin precursor ion in a 5+ charge state. Details are discussed in Example 5.

Ions passed to the first quadrupole (Q1). Several possible insulin precursor ions were observed at Q1. An exemplary Q1 spectra is seen in FIG. 9. Fragmentation studies were conducted on multiply charged insulin precursor ions with m/z of about 1163.32±0.50 (a 5+ ion) and of about 969.56±0.50 (a 6+ ion). Exemplary product ion scans from the fragmentation of each precursor ion are shown in FIGS. 10 and 11, respectively.

Figure 12:
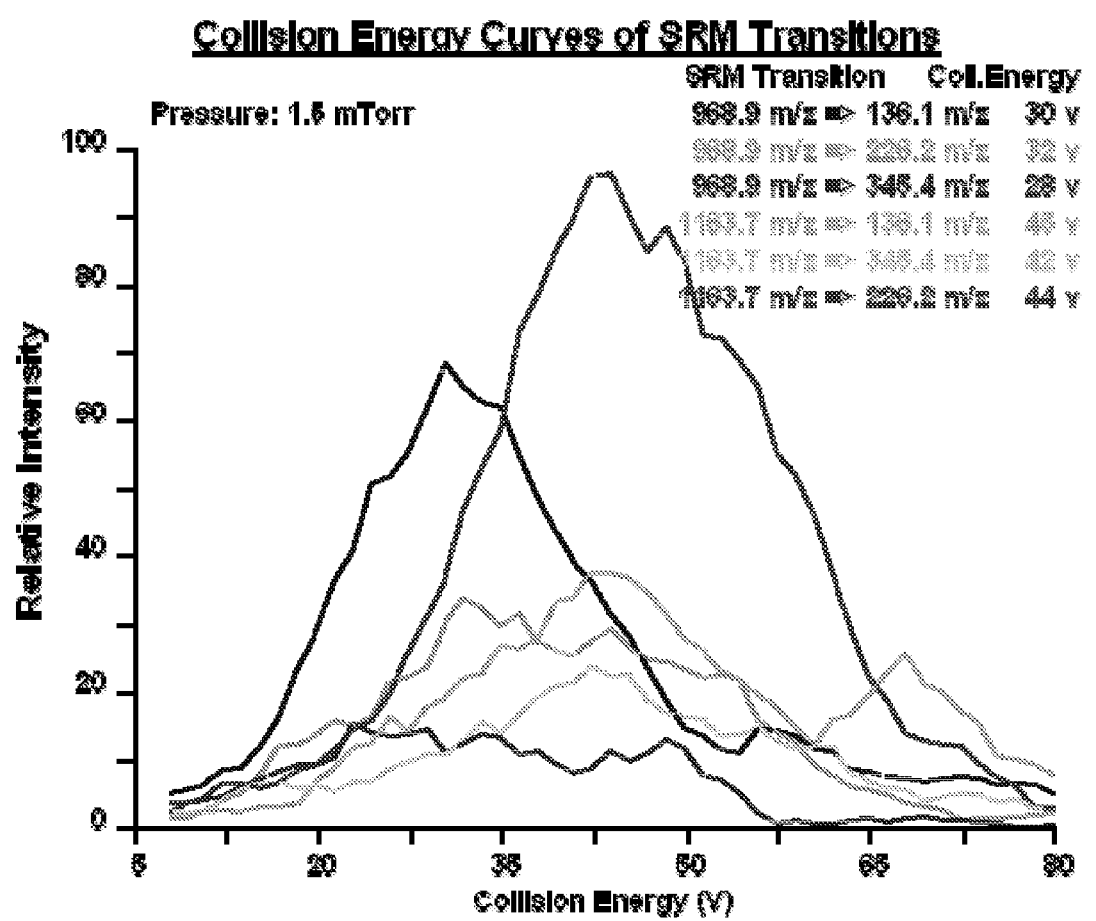
FIG. 12 shows relative intensities of selected fragment ions generated from fragmenting 6+ and 5+ human insulin precursor ions at different collision energies. Details are discussed in Example 5.

The effects of collision energy on the fragmentation patterns from the 5+ and 6+ precursor ions were studied. Each precursor ion was fragmented at collision energies ranging from about 7 eV to about 80 eV, and the relative intensities of three selected fragment ions (m/z of about 135.9±0.50, 226.2±0.50, and 345.3±0.50) were monitored. The results from these studies are demonstrated in FIG. 12. As seen in FIG. 12, the relative intensities of the fragment ions varies significantly depending on the collision energy. Optimal collision energy values for each monitored transition are shown in Table 1.

TABLE 1

Optimal Collision Energy for Exemplary Mass Transitions Observed for Insulin (Positive Polarity-Acidic Conditions)

| Precursor Ion (m/z) | Product Ions (m/z) | Optimal Collision Energy |
|---|---|---|
| 969.56 ± 0.50 (6+) | 135.9 ± 0.50 | 30 eV |
|  | 226.2 ± 0.50 | 32 eV |
|  | 345.4 ± 0.50 | 28 eV |
| 1163.32 ± 0.50 (5+) | 135.9 ± 0.50 | 45 eV |
|  | 226.2 ± 0.50 | 42 eV |
|  | 345.4 ± 0.50 | 44 eV |

For quantitation of insulin by fragmentation of the 6+ ion, precursor ions entering quadrupole 2 (Q2) collided with argon gas at a collision energy of 30 eV to generate ion fragments, which were passed to quadrupole 3 (Q3) for further selection. The following mass transitions were observed for fragmentation of the 969.56±0.50 precursor ion. An exemplary fragmentation spectra collected from a Q3 scan (product ion scan) is shown in FIG. 10.

Of the observed transitions, two were monitored in MRM mode and summed for quantitative analysis: the precursor ion of 969.56±0.50 to 135.9±0.50 and 226.2±0.50 (See Table 2). Although quantitation was accomplished by monitoring two mass transitions, quantitation may be accomplished by monitoring as few as a single mass transition. Conversely, additional mass transitions (including, for example, any other fragment ion observed in FIG. 10) may be selected to replace or augment, in any combination, any of the above monitored transitions. Similarly, although quantitation was accomplished at a collision energy of 30 eV, any collision energy that results in sufficient ion signal may be used and may depend on the identity of the fragment ion(s) being monitored. For example, for the two fragment ions indicated above, a collision energy may be in the range of about 20 to about 50 eV, such as in the range of about 25 to about 40 eV, such as about 28 to 32 eV.

For quantitation of insulin by fragmentation of the 5+ ion, precursor ions entering quadrupole 2 (Q2) collided with argon gas at a collision energy of 49 eV to generate ion fragments, which were passed to quadrupole 3 (Q3) for further selection. The following mass transitions were observed for fragmentation of the 1163.32±0.50 precursor ion. An exemplary fragmentation spectra collected from a Q3 scan (product ion scan) is shown in FIG. 11.

Of the observed transitions, two were monitored in MRM mode and summed for quantitative analysis: the precursor ion of 1163.32±0.50 to 135.9±0.50 and 226.2±0.50 (see Table 2). Although quantitation was accomplished by monitoring two mass transitions, quantitation may be accomplished by monitoring as few as a single mass transition. Conversely, additional mass transitions (including, for example, any other fragment ion observed in FIG. 10) may be selected to replace or augment, in any combination, any of the above monitored transitions. Similarly, although quantitation was accomplished at a collision energy of 49 eV, any collision energy that results in sufficient ion signal may be used and may depend on the identity of the fragment ion(s) being monitored. For example, for the two fragment ions indicated above, a collision energy may be in the range of about 25 to about 70 eV, such as in the range of about 30 to about 60 eV, such as about 35 to 50 eV.

TABLE 2

Exemplary Mass Transitions Monitored for Quantitation of Insulin (Positive Polarity-Acidic Conditions)

| Precursor Ion (m/z) | Product Ions (m/z) | Collision Energy |
| --- | --- | --- |
| 969.56 ± 0.50 (6+) | 135.9 ± 0.50, 226.2 ± 0.50 | 30 eV |
| 1163.32 ± 0.50 (5+) | 135.9 ± 0.50, 226.2 ± 0.50 | 49 eV |

Example 6: Detection and Quantitation of Insulin A Chain and B Chain by Tandem MS Insulin spiked mock serum and stripped serum samples prepared as described in Example 1 were treated with TCEP (tris(2-carboxyethyl)phosphine to reduce insulin's disulfide bridges and separate the A chain and B chain. After disulfide reduction, samples containing the separated A chain and B chain were subjected to the same purification procedure described in Example 2. The resulting insulin A chain and B chain were subjected to MS/MS analysis as described in Example 5. Both analytes were ionized by ESI in positive mode under acidic conditions.

Figure 13:
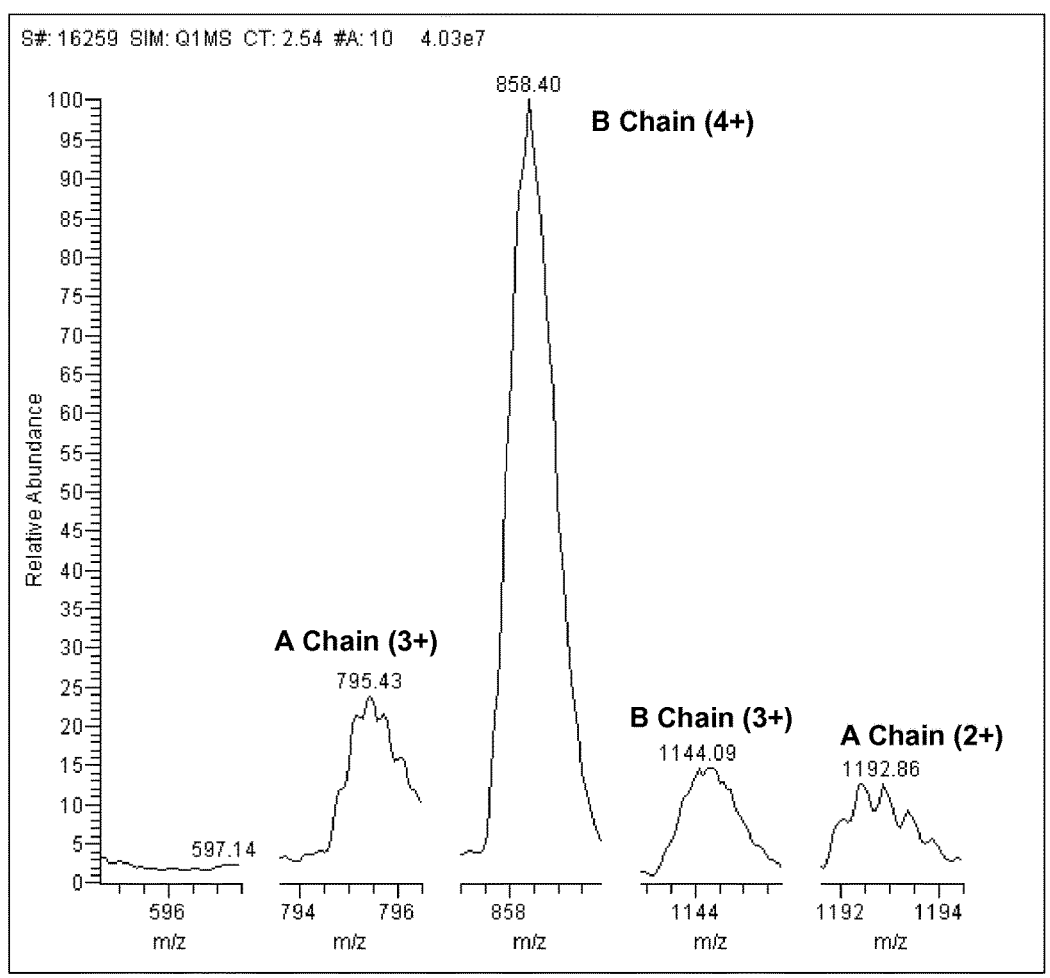
FIG. 13 shows a composite spectra showing two possible human insulin A chain precursor ions (in 2+ and 3+ charge states) and two possible human insulin B chain precursor ions (in 3+ and 4+ charge states). Details are discussed in Example 6.
Figure 14:
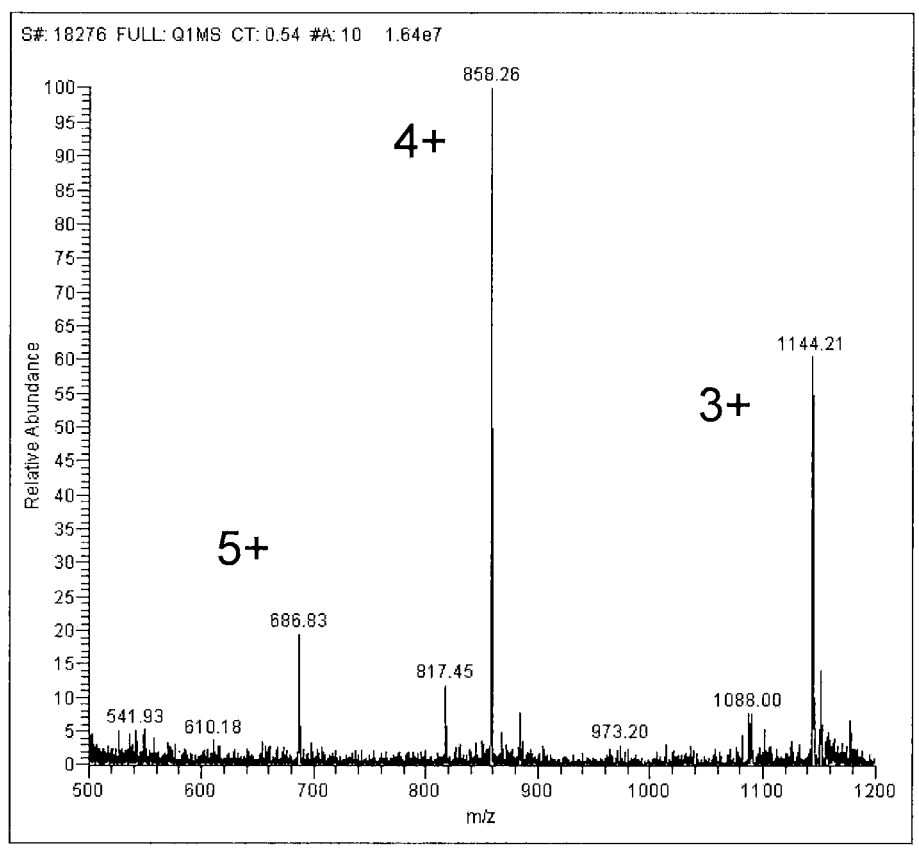
FIG. 14 shows a tandem mass spectrometry Q1 scan showing generation of possible human insulin B chain precursor ions in 3+, 4+, and 5+ charge states. Details are described in Example 6.

Several possible insulin A chain and B chain precursor ions were observed at Q1. A composite spectra showing two possible A chain precursor ions (in 2+ and 3+ charge states) and two possible B chain precursor ions (in 3+ and 4+ charge states) is shown in FIG. 13. These two A chain precursor ions were observed with m/z of about 1192.86±0.50 (2+ ion) and 795.43±0.50 (3+ ion). These two B chain precursor ions were observed with m/z of about 1144.09±0.50 (3+ ion) and 858.40±0.50 (4+ ion). A third possible B chain precursor ion (shown in FIG. 14) was also observed with m/z of about 686.83±0.50 (5+ ion). Fragmentation studies were conducted on all of the above A chain and B chain precursor ions.

Figure 15:
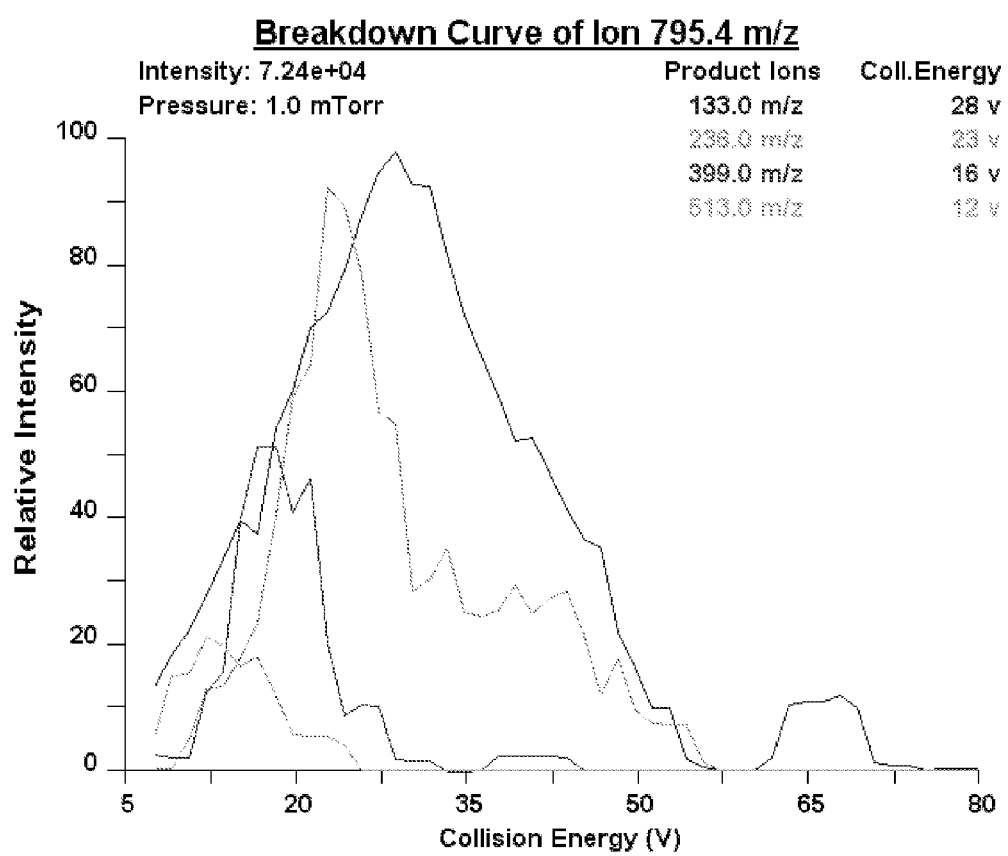
FIG. 15 shows relative intensities of selected fragment ions generated from fragmenting 3+ human insulin A chain precursor ions at different collision energies. Details are discussed in Example 6.

The effects of collision energy on the fragmentation patterns from the A chain 3+ precursor ion (m/z of about 795.43±0.50) were studied. The precursor ion was fragmented at collision energies ranging from about 7 eV to about 80 eV, and the relative intensities of four selected fragment ions (m/z of about 513.0±0.50, 399.0±0.50, 236.0±0.50, and 133.0±0.50) were monitored. The results from these studies are demonstrated in FIG. 15. As seen in FIG. 15, the relative intensities of the fragment ions varies significantly depending on the collision energy. Optimal collision energy values for each monitored transition are shown in Table 3.

TABLE 3

Optimal Collision Energy for Exemplary Mass Transitions Observed for Insulin A Chain 3+ Precursor Ion (Positive Polarity-Acidic Conditions)

| Precursor Ion (m/z) | Product Ions (m/z) | Optimal Collision Energy |
| --- | --- | --- |
| 795.4 ± 0.50 (3+) | 133.0 ± 0.50 | 28 eV |
|  | 236.0 ± 0.50 | 23 eV |
|  | 399.0 ± 0.50 | 16 eV |
|  | 513.0 ± 0.50 | 12 eV |

Insulin quantitation was conducted with A chain precursor ions with m/z of about 1192.86±0.50 (2+ ion) and 795.43±0.50 (3+ ion). Quantitation experiments were conducted with each of the precursor ions. In these quantitation experiments, the 2+ ion (m/z of about 1192.86±0.50) or the 3+ ion (m/z of about 795.43±0.50) was selected as the precursor ion and fragmented at collision energies as shown in Table 3. The following fragment ions were monitored regardless of the precursor ion selected: 513.0±0.50, 399.0 0.50, 236.0±0.50, and 133.0±0.50. Although quantitation was accomplished by monitoring four mass transitions, quantitation may be accomplished by monitoring as few as a single mass transition. Conversely, additional mass transitions (including, for example, any other fragment ion observed) may be selected to replace or augment, in any combination, any of the above monitored transitions.

TABLE 4

Exemplary Mass Transitions Monitored for Quantitation of Insulin A Chain (Positive Polarity-Acidic Conditions)

| Precursor Ion (m/z) | Product Ions (m/z) |
| --- | --- |
| 1192.86 ± 0.50 (2+ ion) | 513.0 ± 0.50, 399.0 ± 0.50, 236.0 ± 0.50, and 133.0 ± 0.50 |
| 795.43 ± 0.50 (3+ ion) | 513.0 ± 0.50, 399.0 ± 0.50, 236.0 ± 0.50, and 133.0 ± 0.50 |

Figure 16:
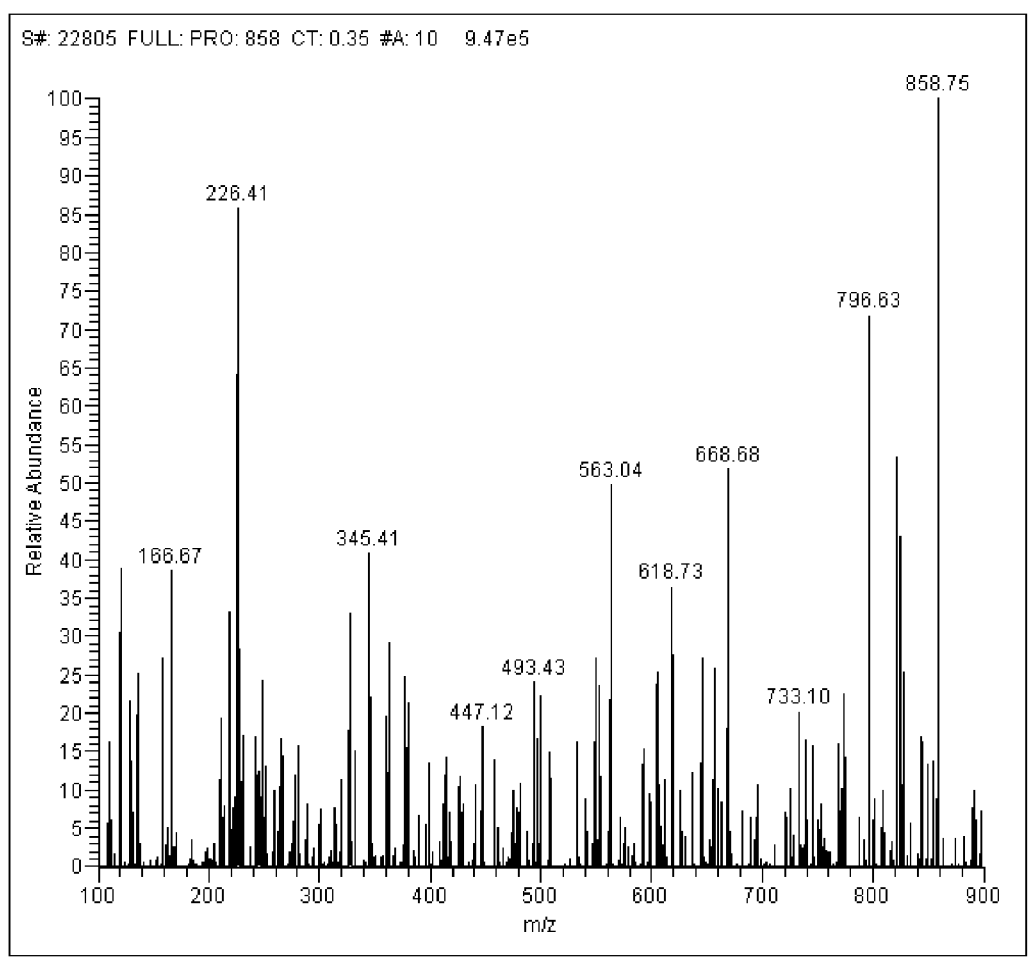
FIG. 16 shows a product ion scan from fragmentation of a human insulin B chain precursor ion in a 4+ charge state. Details are discussed in Example 6.

Insulin quantitation was also conducted with B chain precursor ions with m/z of about 1144.09±0.50 (3+ ion), 858.40±0.50 (4+ ion), and 686.83±0.50 (5+ ion). Quantitation experiments were conducted with each of the precursor ions. In these quantitation experiments, the 3+ ion (m/z of about 1144.09±0.50), the 4+ ion (m/z of about 795.43±0.50), or the 5+ ion (m/z of about 686.83±0.50) was selected as the precursor ion and fragmented at a collision energy of 30 eV. The following fragment ions were monitored regardless of the precursor ion selected: 226.2±0.50 and 345.0±0.50. An exemplary spectra from the fragmentation of the B chain 4+ ion at a collision energy of 30 eV (i.e., a product ion scan)

is shown in FIG. 16. Although quantitation was accomplished by monitoring two mass transitions, quantitation may be accomplished by monitoring as few as a single mass transition. Conversely, additional mass transitions (including, for example, any other fragment ion observed in FIG. 16) may be selected to replace or augment, in any combination, any of the above monitored transitions.

TABLE 5

Exemplary Mass Transitions Monitored for Quantitation of Insulin B Chain (Positive Polarity-Acidic Conditions)

| Precursor Ion (m/z) | Product Ions (m/z) |
|---|---|
| 1144.09 ± 0.50 (3+ ion) | 226.2 ± 0.50, 345.0 ± 0.50 |
| 858.40 ± 0.50 (4+ ion) | 226.2 ± 0.50, 345.0 ± 0.50 |
| 686.83 ± 0.50 (5+ ion) | 226.2 ± 0.50, 345.0 ± 0.50 |

Example 7: Detection and Quantitation of Insulin A Chain (Alkylated) and B Chain (Alkylated) by Tandem MS Insulin spiked mock serum and stripped serum samples were treated with DTT (1,4-dithiothreitol) to generate mock and stripped serum samples containing separated A chains and B chains. Prior to purification, insulin A-chain and B-chain molecules were subjected to carbamidomethylation to fully alkylate each constituent cysteine present in the molecules. In the A chain, four cysteines are alkylated by this process, resulting in a mass increase of about 228.08 amu. In the B chain, two cysteines are alkylated by this process, resulting in a mass increase of about 114.04 amu.

After alkylation of the cysteines, samples containing the alkylated A chain and alkylated B chain were subjected to the same purification procedure described in Example 2. The resulting alkylated A chain and alkylated B chain were subjected to MS/MS analysis as described in Example 5. Both analytes were ionized by ESI in positive mode under acidic conditions.

Several possible alkylated A chain and alkylated B chain precursor ions were observed at Q1. Two possible A chain precursor ions with m/z of about 1306.0±0.50 (2+ ion) and 871.0±0.50 (3+ ion) were selected for fragmentation and quantitation. Three possible alkylated B chain precursor ions with m/z of about 1181.9±0.50 (3+ ion) and 886.40±0.50 (4+ ion) and 709.80±0.50 (5+ ion) were selected for fragmentation and quantitation.

Insulin quantitation was conducted with alkylated A chain precursor ions with m/z of about 1306.0±0.50 (2+ ion) and 871.0±0.50 (3+ ion). Quantitation experiments were conducted with each of the precursor ions. In these quantitation experiments, the 2+ ion (m/z of about 1306.0±0.50) or the 3+ ion (m/z of about 871.0±0.50) was selected as the precursor ion and fragmented at a collision energy of 30 eV. The following fragment ions were monitored regardless of the precursor ion selected: 133.0±0.50, 293.0±0.50, 456.0±0.50, and 570.0±0.50. Although quantitation was accomplished by monitoring four mass transitions, quantitation may be accomplished by monitoring as few as a single mass transition. Conversely, additional mass transitions may be selected to replace or augment, in any combination, any of the above monitored transitions.

TABLE 6

Exemplary Mass Transitions Monitored for Quantitation of Alkylated Insulin A Chain (Positive Polarity-Acidic Conditions)

| Precursor Ion (m/z) | Product Ions (m/z) |
|---|---|
| 1306.0 ± 0.50 (2+ ion) | 133.0 ± 0.50, 293.0 ± 0.50, 456.0 ± 0.50, and 570.0 ± 0.50 |
| 871.0 ± 0.50 (3+ ion) | 133.0 ± 0.50, 293.0 ± 0.50, 456.0 ± 0.50, and 570.0 ± 0.50 |

Insulin quantitation was also conducted with alkylated B chain precursor ions at about 1181.9±0.50 (3+ ion), 886.9±0.50 (4+ ion), and 709.8±0.50 (5+ ion). Quantitation experiments were conducted with each of the precursor ions. In these quantitation experiments, the 3+ ion (m/z of about 1181.9±0.50), the 4+ ion (m/z of about 886.9±0.50), or the 5+ ion (m/z of about 709.8±0.50) was selected as the precursor ion and fragmented at a collision energy of 30 eV. The following fragment ions were monitored regardless of the precursor ion selected: 226.2±0.50 and 345.0±0.50. Although quantitation was accomplished by monitoring two mass transitions, quantitation may be accomplished by monitoring as few as a single mass transition. Conversely, additional mass transitions may be selected to replace or augment, in any combination, any of the above monitored transitions.

TABLE 7

Exemplary Mass Transitions Monitored for Quantitation of Alkylated Insulin B Chain (Positive Polarity-Acidic Conditions)

| Precursor Ion (m/z) | Product Ions (m/z) |
|---|---|
| 1181.9 ± 0.50 (3+ ion) | 226.2 ± 0.50, 345.0 ± 0.50 |
| 886.9 ± 0.50 (4+ ion) | 226.2 ± 0.50, 345.0 ± 0.50 |
| 709.8 ± 0.50 (5+ ion) | 226.2 ± 0.50, 345.0 ± 0.50 |

Example 8: Preparation of Human Samples for Insulin Quantitation by Quantitation of Insulin B Chain Two internal standard solutions were used in the quantitation of insulin in human samples. The first internal standard solution was prepared with bovine insulin dissolved in 0.2% formic acid in water to a concentration of 10 pmol/μL. 30 μL of this solution was then diluted with 500 mL of a Base/Extraction solution containing 1.5 M Tris Base and ethanol at a ratio of 15:85. The second internal standard solution was prepared with isotopically labeled human insulin B chain (labeled with a proline with five $^{13}$C and one $^{15}$N) by dissolving 1 mg of the peptide in 1 mL of 0.2% formic acid in water. 5 μL of this concentrated solution was diluted with 1000 μL of water to prepare the second internal standard solution.

Previously frozen human serum samples thawed, allowed to come to room temperature, and vortexed thoroughly. Once thawed, 150 μL of each sample was added to 350 μL of the Base/Extraction solution spiked with bovine insulin. The resulting mixture was vortexed at a speed of 1000 rpm for two minutes, and incubated for 60±5 minutes in a −20° C. freezer allowing a precipitate to form. After incubation, the samples were centrifuged at 5500 rpm for 10 minutes. 250 μl of the supernatant from each sample were then transferred to a 96-MicroLiter plate. 2 mL of TCEP reducing solution (Thermo Scientific catalog #77720) was then mixed with 100 μL of the second internal standard solution, and 20

µL of this mixture was added to each sample in the 96-MicroLiter plate. The samples were again vortexed at a speed of 1000 rpm for 2 minutes, and incubated for 60±5 minutes in a 37° C. incubator to allow reduction of insulin in the sample to occur, and any intact insulin present in the samples to separate into A and B chains. The samples were then incubated for 10 minutes in a −20° C. freezer allowing a precipitate to form. The precipitated samples were again centrifuged at 5500 rpm for 10 minutes. 225 of the supernatant from each sample was then subjected to enrichment via SPE and HPLC prior to MS/MS analysis.

Example 9: Enrichment of Insulin B Chain from Human Samples Prior to Mass Spectrometry Sample injection of the processed serum samples prepared in Example 8 was performed with a Cohesive Technologies Aria TX-420 system using Aria OS V 1.6 or newer software.

225 µL of each sample were introduced into a Waters Oasis HLB (25 µm, 2.1×20 mm), on-line solid phase extraction (SPE) column. The SPE column retained insulin B chains while letting other proteins and large molecules flow through. The retained insulin B chains were washed with 0.2% formic acid.

The insulin B chains were then eluted off the extraction column with 35% acetonitrile in 0.2% formic acid with 0.025% isopropanol and onto the analytical column equipped with a guard cartridge (Michrom Bioresources 300 Armstrong Magic C4 (2.1×50 mm, 5 µm particle size) analytical column and Phenomenex Security Guard column cartridge (Phenomenex P/N AHO-4286)). An HPLC gradient was applied to the guard/analytical columns, to separate insulin from other analytes contained in the sample. Mobile phase A was 0.2% formic acid in water and mobile phase B was 0.2% formic acid in acetonitrile with 2.5% isopropanol. The HPLC gradient started with a 12.0% organic gradient which was ramped to 42% in approximately 90 seconds.

The insulin enriched samples were then subjected to MS/MS for quantitation of insulin.

Example 10: Detection and Quantitation of Insulin B Chain from Human Serum by Tandem MS MS/MS was performed using a Thermo TSQ Vantage MS/MS system (Thermo Electron Corporation). The following software programs, all from Thermo Electron, were used in the Examples described herein: TSQ Vantage V 2.0.0 or newer, Xcalibur V 2.0 or newer, and LCQuan V 2.5 or newer. Liquid solvent/analyte exiting the analytical column flowed to a heated ESI source interface of the MS/MS analyzer. The solvent/analyte mixture was converted to vapor in the heated tubing of the interface. Analytes were ionized by ESI in positive ion mode under acidic conditions.

Figure 17:
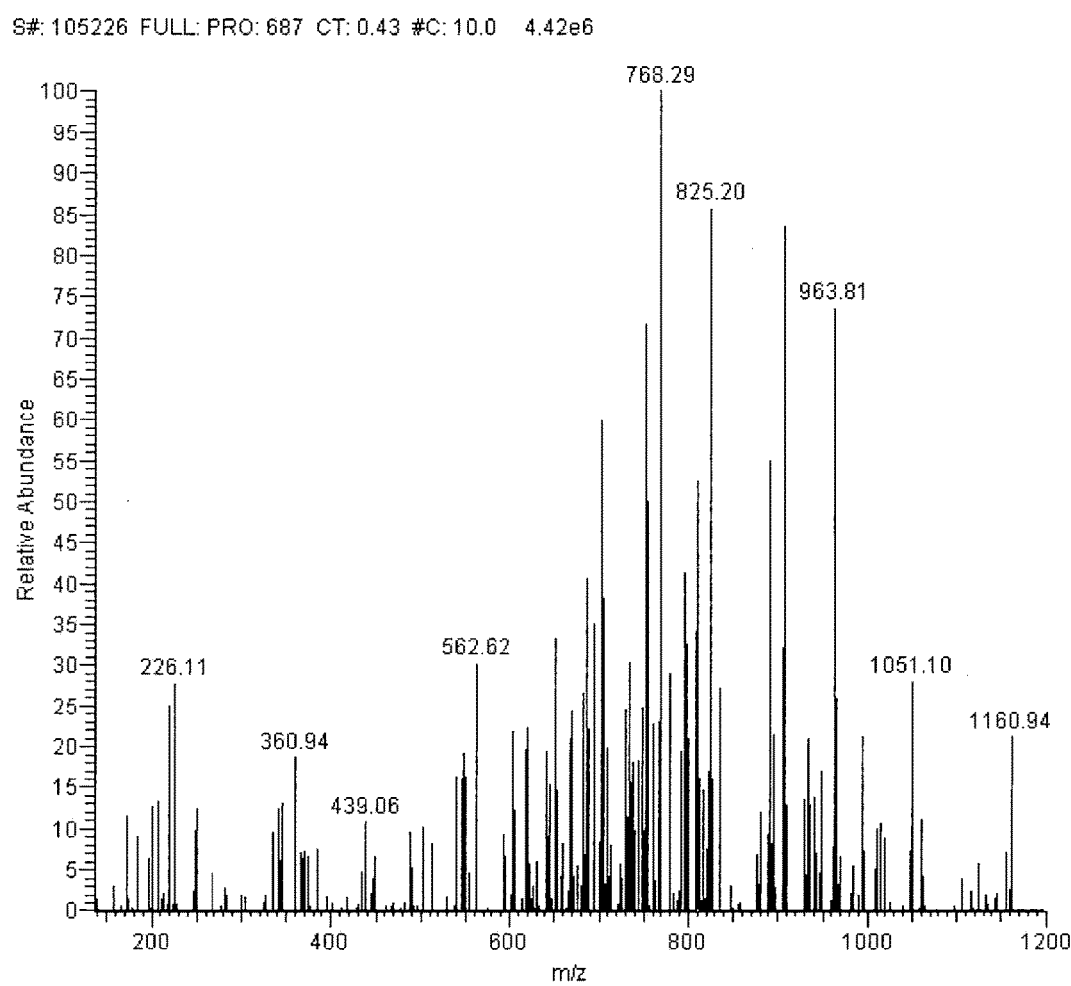
FIG. 17 shows a product ion scan from fragmentation of a human insulin B chain precursor ion in a 3+ charge state. Details are discussed in Example 10.

As described above in Example 6, several possible insulin B chain precursor ions were observed at Q1. The insulin B chain precursor ion with m/z of about 686.83±0.50 (5+ ion) was selected for fragmentation. Fragmentation studies showed a number of insulin B chain fragment ions. An exemplary fragmentation spectra is shown in FIG. 17.

The effects of collision energy on the fragmentation patterns from the human insulin B chain 5+ precursor ion (m/z of about 686.9±0.50) were studied. The precursor ion was fragmented at collision energies ranging from about 7 V to about 80 V, and the relative intensities of five selected fragment ions (m/z of about 906.0±0.50, 825.0±0.50, 768.5±0.50, 753.0±0.50, and 703.0±0.50) were monitored. The results from these studies are demonstrated in FIG. 18.

Figure 18:
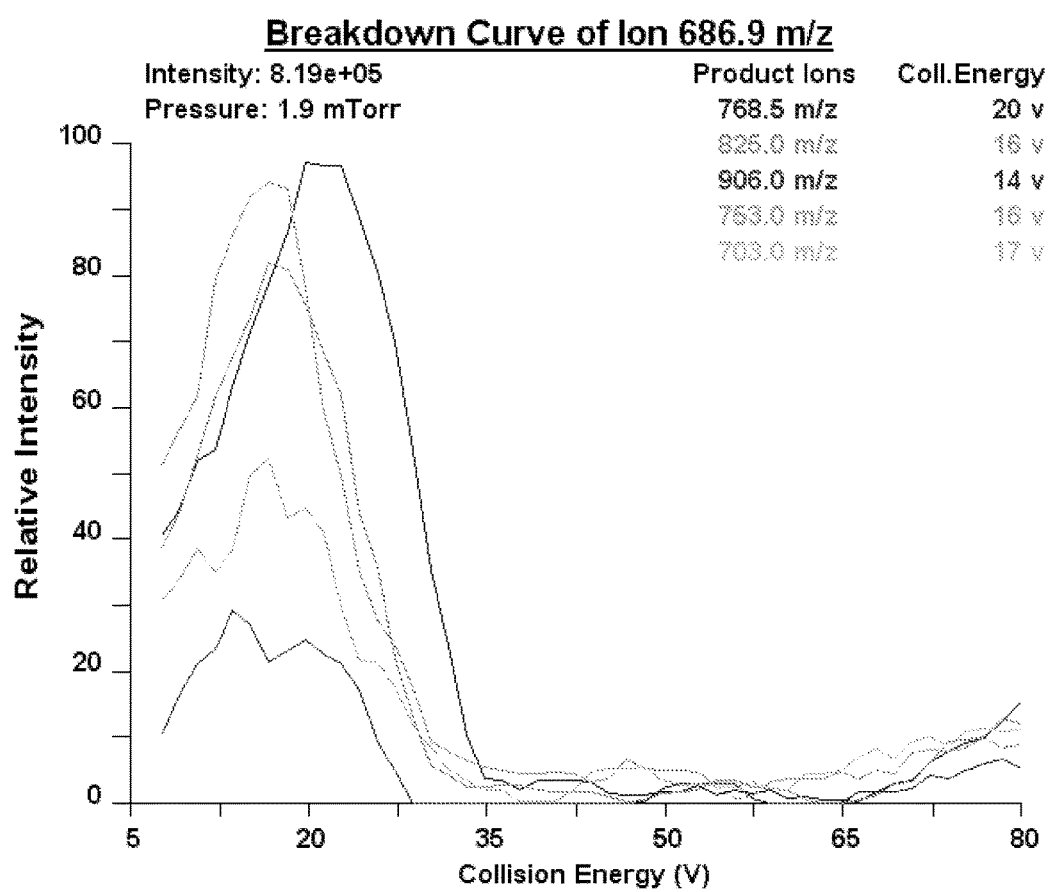
FIG. 18 shows relative intensities of selected fragment ions generated from fragmenting 3+ human insulin B chain precursor ions at different collision energies. Details are discussed in Example 10.

As seen in FIG. 18, the relative intensities of the fragment ions varies significantly depending on the collision energy. Approximate optimal collision energy values for each monitored transition are shown in Table 8.

TABLE 8

Optimal Collision Energy for Exemplary Mass Transitions Observed for Human Insulin B Chain 5+ Precursor Ion (Positive Polarity-Acidic Conditions)

| Precursor Ion (m/z) | Product Ions (m/z) | Optimal Collision Energy (approximately) |
|---|---|---|
| 686.9 ± 0.50 (5+) | 703.0 ± 0.50 | 17 V |
|  | 753.0 ± 0.50 | 16 V |
|  | 768.5 ± 0.50 | 20 V |
|  | 825.0 ± 0.50 | 16 V |
|  | 906.0 ± 0.50 | 14 V |

Human insulin B chain fragment ions with m/z of about 768.5±0.50 and 753.2±0.50 were selected for use in quantitation. Similar studies were conducted with bovine insulin (internal standard 1) and isotopically labeled insulin B chain (internal standard 2), both described in Example 8. Mass transitions monitored for each type of insulin B chain selected for use in further quantitation studies are shown in Table 9.

TABLE 9

Exemplary Mass Transitions Monitored for Quantitation of Insulin B Chain (Positive Polarity-Acidic Conditions)

| Analyte | Precursor Ion (m/z) | Product Ions (m/z) |
|---|---|---|
| Human Insulin B Chain | 686.9 ± 0.50 (5+ ion) | 768.5 ± 0.50, 753.2 ± 0.50 |
| Bovine Insulin B Chain (I.S. 1) | 680.8 ± 0.50 (5+ ion) | 768.5 ± 0.50, 738.3 ± 0.50 |
| Isotopically Labeled Human Insulin B Chain (I.S. 2) | 688.1 ± 0.50 (5+ ion) | 768.5 ± 0.50, 756.0 ± 0.50 |

Although quantitation was accomplished by monitoring two mass transitions for each of the insulin B chains shown in Table 8, quantitation of any of the indicated analytes may be accomplished by monitoring as few as a single mass transition. Conversely, additional mass transitions (including, for example, any other human insulin B chain fragment ion observed in FIG. 17) may be selected to replace or augment, in any combination, any of the above monitored transitions.

Example 11: Intra-Assay and Inter-Assay Precision, Reproducibility, and Accuracy Studies Intra- and inter-assay precision, reproducibility, and accuracy studies of the assay described in Examples 8-10 were conducted with five QC pools made from stripped serum (Biocell Laboratories Inc., 1131-00, lot HHP03) spiked with human insulin at 8, 12, 20, 40, and 80 µIU/mL, to cover the presumptive reportable range of the assay.

Eight replicates from each of the five QC pools were analyzed in a single assay to determine the coefficient of variation (CV) of a sample within an assay. Data resulting from these studies are shown in Table 10. Statistics performed on the results demonstrated that the reproducibility (CV) for the five QC pools ranged from 3.0 to 7.9%, all within acceptable levels (i.e., ≤15% CV, except for the LOQ level where ≤20% CV is acceptable). Further analysis of the data presented in Table 10 revealed intra-assay accuracies of each pool within the acceptable range of 80-120%.

TABLE 10

Intra-Assay Variation and Accuracy

| Replicate | 1 | 2 | 3 | 4 | 5 | 6 | 7 | 8 | mean | SD | CV | accuracy |
|---|---|---|---|---|---|---|---|---|---|---|---|---|
| 8 uIU/mL  | 6.9  | 5.7  | 6.3  | 6.2  | 6.7  | 5.9  | 6.9  | 6.3  | 6.4  | 0.4  | 7.0 | 80.0 |
| 12 uIU/mL | 10.9 | 10.6 | 12.7 | 10.7 | 10.5 | 11.8 | 10.8 | 10.5 | 11.1 | 0.87 | 7.9 | 92.2 |
| 20 uIU/mL | 17.5 | 16   | 17   | 17.4 | 16.7 | 19.1 | 17.3 | 17.4 | 17.3 | 1.04 | 6.0 | 86.5 |
| 40 uIU/mL | 36   | 36.9 | 33.1 | 36.9 | 35.9 | 35.5 | 33   | 33   | 35.0 | 1.40 | 4.0 | 87.6 |
| 80 uIU/mL | 74.3 | 76.6 | 74.1 | 72.2 | 71.7 | 70.3 | 72.3 | 78   | 73.7 | 2.25 | 3.0 | 92.1 |

To investigate inter-assay variation, eight replicates from each of the five QC pools were analyzed on five different days. Data resulting from these studies are shown in Table 11. The inter-assay variation (% CV) for the pools ranged from 7.1 to 14.0%. The overall variations for the targeted insulin levels at 8, 12, 20, 40, and 80 μIU/mL were 14.0%, 10.2%, 10.0%, 7.5%, and 7.1%, respectively. Analysis of all pools met the requirement for acceptable reproducibility of ≤15% CV, except for the LOQ level where ≤20% CV is acceptable. Further analysis of the data presented in Table 11 revealed inter-assay accuracies of each pool within the acceptable range of 80-120%.

defined as four standard deviations from the zero concentration. For selectivity testing, blank samples of the appropriate biological matrix (stripped serum) were obtained, tested for interference, and analyzed by the method described in Examples 8-10. Blank stripped serum samples were measured 14 times. Results of these studies were statistically analyzed, giving a LOB of 1.4 μIU/mL and a LOD of 1.8 μIU/mL.

The LLOQ is the point where measurements become quantitatively meaningful. The analyte response at this LLOQ is identifiable, discrete and reproducible with a

TABLE 11

Inter-Assay Variation and Accuracy

| QC Pool (uIU/mL) | Day | 1 | 2 | 3 | 4 | 5 | 6 | 7 | 8 | mean | SD | CV | accuracy |
|---|---|---|---|---|---|---|---|---|---|---|---|---|---|
| 8  | 1 | 6.9  | 5.7  | 6.3  | 6.2  | 6.7  | 5.9  | 6.9  | 6.3  | 6.4  | 0.4 | 7.0  | 80.0  |
|    | 2 | 7.2  | 6.6  | 6.9  | 6.2  | 6.9  | 8.5  | 7.7  | 6.3  | 7.0  | 0.8 | 10.8 | 88.0  |
|    | 3 | 8.5  | 9.5  | 9.5  | 8.2  | 8.3  | 7.7  | 8.6  | 7.6  | 8.5  | 0.7 | 8.5  | 106.0 |
|    | 4 | 6.7  | 6.2  | 5.7  | 6.1  | 7    | 6.1  | 7.4  | 7.6  | 6.6  | 0.7 | 10.4 | 82.5  |
|    | 5 | 7.6  | 8.1  | 7.9  | 7.5  | 8.5  | 7.7  | 8.9  | 8    | 8.0  | 0.5 | 5.9  | 100.3 |
|    | mean | | | | | | | | | 7.3 | 1.0 | 14.0 | 91.3 |
| 12 | 1 | 10.9 | 10.6 | 12.7 | 10.7 | 10.5 | 11.8 | 10.8 | 10.5 | 11.1 | 0.8 | 7.1  | 92.2  |
|    | 2 | 9.5  | 10.1 | 8.8  | 11.9 | 10   | 10.1 | 9.4  | 10.4 | 10.0 | 0.9 | 9.1  | 83.5  |
|    | 3 | 11.2 | 11.8 | 11.4 | 12.7 | 11.2 | 11.9 | 11.3 | 11.8 | 11.6 | 0.5 | 4.5  | 97.1  |
|    | 4 | 8.4  | 9.4  | 8    | 10.1 | 11.5 | 11.7 | 11.2 | 10.8 | 10.1 | 1.4 | 13.9 | 84.5  |
|    | 5 | 11.7 | 11.2 | 10.8 | 11.9 | 11.4 | 14.4 | 11.9 | 11.4 | 11.8 | 1.1 | 9.2  | 98.6  |
|    | mean | | | | | | | | | 10.9 | 1.2 | 10.2 | 91.2 |
| 20 | 1 | 17.5 | 16   | 17   | 17.4 | 16.7 | 19.1 | 17.3 | 17.4 | 17.3 | 0.9 | 5.1  | 86.5  |
|    | 2 | 16.9 | 14.6 | 18   | 16.9 | 17.5 | 16   | 18.2 | 17.4 | 16.9 | 1.2 | 6.9  | 84.7  |
|    | 3 | 15.9 | 17   | 17.1 | 16.4 | 15.7 | 16.1 | 16.1 | 19.3 | 16.7 | 1.2 | 7.0  | 83.5  |
|    | 4 | 15.5 | 17.4 | 18.6 | 16.7 | 17.4 | 19.6 | 18.7 | 16.8 | 17.6 | 1.3 | 7.5  | 87.9  |
|    | 5 | 17.1 | 16.9 | 16.9 | 15.3 | 24.6 | 21.6 | 18.0 | 17.4 | 18.5 | 3.1 | 16.5 | 92.4  |
|    | mean | | | | | | | | | 17.4 | 1.7 | 10.0 | 87.0 |
| 40 | 1 | 36   | 36.9 | 33.1 | 36.9 | 35.9 | 35.5 | 33   | 33   | 35.0 | 1.7 | 4.9  | 87.6  |
|    | 2 | 30.8 | 38.5 | 36.8 | 32.3 | 33.6 | 34   | 34.5 | 30.4 | 33.9 | 2.8 | 8.2  | 84.7  |
|    | 3 | 39.1 | 36.8 | 33.2 | 37   | 36.4 | 37.8 | 38.4 | 38.9 | 37.2 | 1.9 | 5.1  | 93.0  |
|    | 4 | 41.4 | 36.3 | 37.6 | 33.3 | 34.6 | 36.7 | 36.4 | 36.1 | 36.6 | 2.4 | 6.5  | 91.4  |
|    | 5 | 34.3 | 30.8 | 29.5 | 33.1 | 34.3 | 33.7 | 32.5 | 33.7 | 32.7 | 1.7 | 5.3  | 81.8  |
|    | mean | | | | | | | | | 35.1 | 2.6 | 7.5  | 87.7 |
| 80 | 1 | 74.3 | 76.6 | 74.1 | 72.2 | 71.7 | 70.3 | 72.3 | 78   | 73.7 | 2.6 | 3.5  | 92.1  |
|    | 2 | 75.5 | 77.4 | 72.7 | 72.8 | 71.9 | 67.1 | 69.2 | 74.5 | 72.6 | 3.3 | 4.6  | 90.8  |
|    | 3 | 88.2 | 77.3 | 85.0 | 87.1 | 85.4 | 81.1 | 82.9 | 82.8 | 83.7 | 3.5 | 4.2  | 104.6 |
|    | 4 | 72.3 | 76.4 | 74.3 | 78.7 | 73.5 | 71   | 84.9 | 71.8 | 75.4 | 4.6 | 6.1  | 94.2  |
|    | 5 | 74.8 | 85   | 77.2 | 84.1 | 82.1 | 81   | 76   | N/A  | 80.0 | 4.0 | 5.1  | 100.0 |
|    | mean | | | | | | | | | 77.0 | 5.5 | 7.1  | 96.3 |

Example 12: Analytical Sensitivity: Limit of Blank (LOB), Limit of Detection (LOD), and Limit of Quantitation (LOQ)

Figure 19:
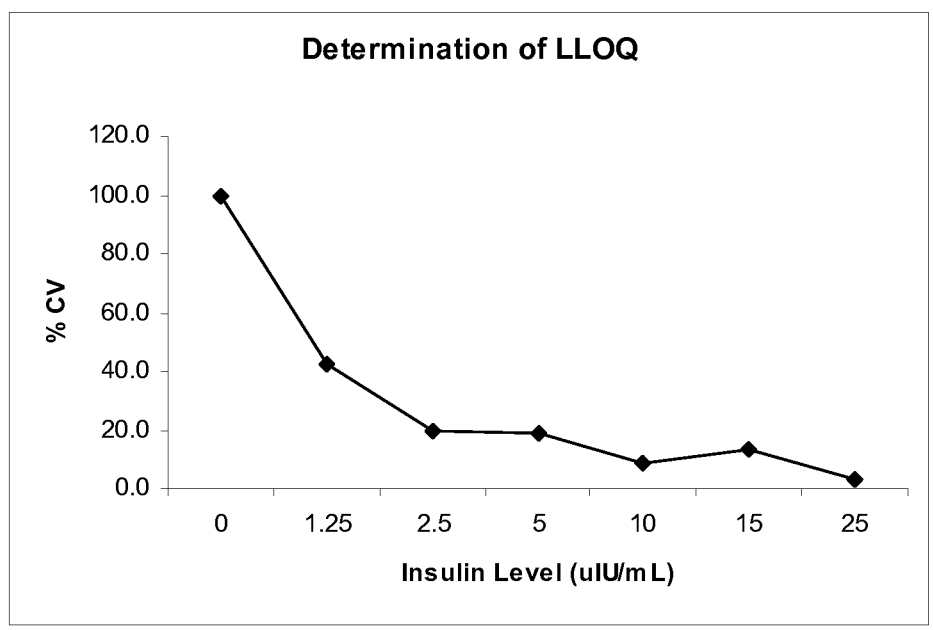
FIG. 19 shows a plot used to assess LLOQ of human insulin in patient serum samples by tandem mass spectrometry of human insulin B chain. Details are discussed in Example 12.

Selectivity is the ability of an analytical method to differentiate and quantify the analyte in the presence of other components in the sample. LOB and LOD are both indicators that a measured value is larger than the uncertainty associated with its measurement. The LOB is defined as two standard deviations from the zero concentration. The LOD is precision of 20% and an accuracy of 80% to 120%. The LLOQ was determined by assaying six stripped serum specimens spiked with human insulin at concentrations near the expected LLOQ (1.25, 2.5, 5, 10, 15, and 25 μIU/mL, then evaluating the intra-assay reproducibility of seven runs. Data from these studies were analyzed and plotted (shown in FIG. 19) and the LLOQ was determined from the curve to be 3 μIU/mL, the lowest concentration that yields acceptable performance where the 95% confidence interval for the CV remains below 20%.

Example 13: Assay Reportable Range and Linearity

Figure 20:
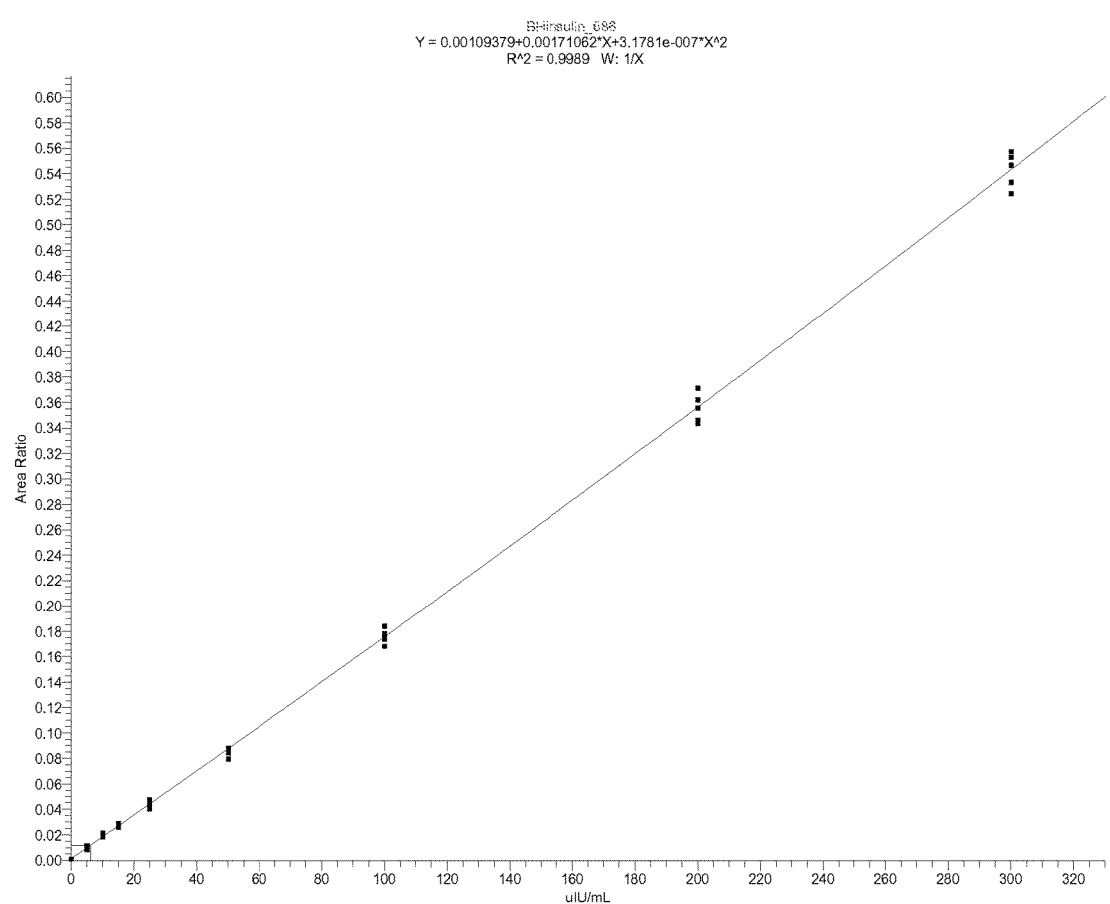
FIG. 20 shows a plot of the linearity of quantitation of human insulin in spiked stripped serum samples measured with tandem mass spectrometry of human insulin B chain. Details are described in Example 13.

To establish the linear range of the assay described in Examples 8-10, eight spiked stripped serum samples (at human insulin concentrations of 5, 10, 15, 25, 50, 100, 200, and 300 µIU/mL) were prepared and analyzed on five separate days. A weighted (1/X) linear regression from five consecutive runs yielded coefficient correlations of 0.995 or greater, with an accuracy of ±20%, revealing a quantifiable range of 5 to 300 µIU/mL. An exemplary calibration curve is shown in FIG. 20.

Example 14: Specimen Type Studies

Matrix specificity was evaluated by collecting ten human patient pools in six different types of BD Vacutainer™ tubes (plain serum, SST, EDTA plasma, sodium heparin plasma, lithium heparin plasma, and sodium citrate plasma). Insulin from samples from each pool were then extracted and analyzed according to the methods described in Examples 8-10. These studies indicated that sodium citrate plasma samples were unacceptable for analysis, but that all other sample types were acceptable.

Example 15: Interference Studies

The effects of hemolysis interference on insulin determination were evaluated by spiking different levels of insulin in low, medium, and high hemolytic patient samples. Insulin was then extracted and analyzed according to the methods described in Examples 8-10. Data from these studies indicated that acceptable results (i.e., within 80-120% accuracy) were obtained for light and moderate hemolysis samples. High hemolysis samples were not acceptable.

The effects of lipemia interference on insulin determination were evaluated by spiking different levels of insulin in low, medium, and high lipemic patient samples. Insulin was then extracted and analyzed according to the methods described in Examples 8-10. Data from these studies indicated that acceptable results (i.e., within 80-120% accuracy) were obtained for all levels of lipemia.

The effects of bilirubin interference on insulin determination were evaluated by spiking different levels of insulin in low, medium, and high icteric patient samples. Insulin was then extracted and analyzed according to the methods described in Examples 8-10. Data from these studies indicated that acceptable results (i.e., within 80-120% accuracy) were obtained for all levels of bilirubin.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of insulin in a biological sample by tandem mass spectrometry, the method comprising:
    (a) subjecting the sample to conditions suitable to generate insulin B chains from insulin;
    (b) processing the sample from step (a) to obtain a fraction enriched in insulin B chains;
    (c) subjecting the enriched insulin B chains to an ionization source under conditions suitable to generate one or more insulin B chain ions detectable by mass spectrometry;
    (d) selecting and fragmenting a precursor ion with a mass to charge ratio (m/z) of 686.8±0.5; and
    (e) determining the amount of one or more insulin B chain fragment ions that result from step (d) by tandem mass spectrometry,
    wherein the amount of ions determined in step (d) is related to the amount of insulin in said sample.

2. The method of claim 1, wherein said processing of step (b) comprises enriching insulin B chains by solid phase extraction (SPE).

3. The method of claim 1, wherein said processing of step (b) comprises enriching insulin B chains by high performance liquid chromatography (HPLC).

4. The method of claim 1, wherein said biological sample comprises a human plasma or serum sample.

5. The method of claim 1, wherein said ionization source is an electrospray (ESI) ionization source.

6. The method of claim 1, wherein said sample is subjected to acidic conditions prior to ionization in positive ion mode.

7. The method of claim 6, wherein subjecting said sample to acidic conditions comprises subjecting said sample to formic acid.

8. The method of claim 1, wherein said one or more ions determined in step (d) comprise one or more fragment ions selected from the group consisting of ions with mass to charge ratios (m/z) of 906.0±0.5, 825.0±0.5, 768.5±0.5, 753.0±0.5, and 703.0±0.5.

9. The method of claim 1, wherein the ions determined in step (d) comprise one or more ions from the group consisting of ions with m/z of 768.5±0.5 and 753.0±0.5.

10. The method of claim 1, wherein said fragmenting is conducted with a collision energy within the range of 10 to 25 eV, inclusive.

\* \* \* \* \*